United States Patent
Kim et al.

(10) Patent No.: US 11,364,244 B2
(45) Date of Patent: Jun. 21, 2022

(54) COMPOSITIONS FOR TREATMENT OF MUSCULAR DISORDERS

(71) Applicant: ONCOCROSS CO., LTD., Seoul (KR)

(72) Inventors: Yi-Rang Kim, Sejong (KR); Jin-Woo Choi, Gyeonggi-do (KR)

(73) Assignee: ONCOCROSS CO., LTD., Seoul (KR)

( * ) Notice: Subject to any disclaimer, the term of this patent is extended or adjusted under 35 U.S.C. 154(b) by 23 days.

(21) Appl. No.: 16/607,266

(22) PCT Filed: Apr. 17, 2019

(86) PCT No.: PCT/KR2019/004631
§ 371 (c)(1),
(2) Date: Oct. 22, 2019

(87) PCT Pub. No.: WO2019/208968
PCT Pub. Date: Oct. 31, 2019

(65) Prior Publication Data
US 2020/0246343 A1    Aug. 6, 2020

(30) Foreign Application Priority Data

Apr. 25, 2018 (KR) .................. 10-2018-0047957

(51) Int. Cl.
| | | |
|---|---|---|
| A61K 31/522 | (2006.01) | |
| A61K 31/197 | (2006.01) | |
| A61K 31/437 | (2006.01) | |
| A61K 45/06 | (2006.01) | |
| A61K 31/19 | (2006.01) | |
| A61K 31/137 | (2006.01) | |
| A23L 33/10 | (2016.01) | |
| A61P 21/00 | (2006.01) | |
| A61P 21/04 | (2006.01) | |

(52) U.S. Cl.
CPC .......... *A61K 31/522* (2013.01); *A61K 31/197* (2013.01); *A61K 31/437* (2013.01); *A61K 45/06* (2013.01)

(58) Field of Classification Search
CPC .. A61K 31/522; A61K 31/197; A61K 31/437; A61K 45/06; A61K 31/19; A61K 31/137; A61P 21/04; A61P 21/00; A23L 33/10; A23V 2002/00; A23V 2200/316
See application file for complete search history.

(56) References Cited

U.S. PATENT DOCUMENTS

| | | | |
|---|---|---|---|
| 5,554,647 A | 9/1996 | Perricone | |
| 9,572,810 B2 | 2/2017 | Lange et al. | |
| 2002/0099068 A1 | 7/2002 | Ritzeler et al. | |
| 2003/0003162 A1* | 1/2003 | Rath | A61K 33/06 424/682 |
| 2006/0057188 A1* | 3/2006 | Gaetani | A61K 31/22 514/23 |
| 2006/0166978 A1 | 7/2006 | Ritzeler et al. | |
| 2009/0298852 A1* | 12/2009 | Francas | A61P 25/00 514/255.04 |
| 2011/0313041 A1* | 12/2011 | Minge | A61P 25/06 426/443 |
| 2014/0235656 A1* | 8/2014 | Karavas | A61K 9/2027 514/263.34 |
| 2017/0042866 A1* | 2/2017 | Zaid | A61K 31/12 |

FOREIGN PATENT DOCUMENTS

| | | |
|---|---|---|
| JP | 2003527394 A | 9/2003 |
| JP | 2013532661 A | 8/2013 |
| WO | 2005/009370 A2 | 2/2005 |
| WO | 2012012682 A2 | 1/2012 |
| WO | 2017203540 A1 | 11/2017 |
| WO | 2017/218905 A1 | 12/2017 |

OTHER PUBLICATIONS

Christ, G. J., "The pharmacology of regenerative medicine." Pharmacological reviews 65.3 (2013): 1091-1133.*
Dalakas, M. C., "Inflammatory muscle diseases." New England Journal of Medicine 372.18 (2015): 1734-1747.*
Roschek, B., "Nettle extract (Urtica dioica) affects key receptors and enzymes associated with allergic rhinitis." Phytotherapy Research: An International Journal Devoted to Pharmacological and Toxicological Evaluation of Natural Product Derivatives 23.7 (2009): 920-926.*
Abe, A.,"Harmol induces autophagy and subsequent apoptosis in U251MG human glioma cells through the downregulation of survivin." Oncology Reports 29.4 (2013): 1333-1342.*

* cited by examiner

*Primary Examiner* — John M Mauro

(74) *Attorney, Agent, or Firm* — Potomac Law Group, PLLC

(57) ABSTRACT

The present invention relates to a pharmaceutical composition for prevention or treatment of a muscular disease, the composition comprising dimenhydrinate, harmol and/or calcium pantothenate as active ingredients. Application of dimenhydrinate, harmol, and calcium pantothenate individually has an effect of promoting myoblast proliferation and differentiation. In particular, the combination thereof has the effect of synergistically increasing the effect of promoting myoblast proliferation and differentiation. Thus, dimenhydrinate, harmol and/or calcium pantothenate may be usefully used alone or in combination for the prevention or treatment of muscular diseases, in particular sarcopenia.

16 Claims, 20 Drawing Sheets

∷ Early restoration at OC-501, 504 combination in cardiotoxin injection mouse

COMPOSITIONS FOR TREATMENT OF MUSCULAR DISORDERS

CROSS REFERENCE TO RELATED APPLICATIONS

This application is a § 371 National Stage of International Application No. PCT/KR2019/004631 filed Apr. 17, 2019, claiming priority to Korean Patent Application No. 10-2018-0047957 filed Apr. 25, 2018.

TECHNICAL FIELD

The present disclosure relates to a pharmaceutical composition for treatment of a muscular disease. More particularly, the present disclosure relates to a pharmaceutical composition for preventing or treating a muscular disease, the composition comprising dimenhydrinate, harmol and/or calcium pantothenate as an active ingredient.

BACKGROUND ART

A skeletal muscle makes up the largest part of the human body, and accounts for 40 to 50% of a total body weight and plays an important role in various metabolic functions in the body, including energy homeostasis and heat generation. An amount of a human muscle decreases by more than 1% annually after an age 40 and then to a 50% of a maximum muscle amount at an age 80. This muscle loss in the old age is recognized as the most important factor that impairs overall physical functions. As the aging progresses, a muscle and fat content changes and a skeletal distortion occurs. A prevalence of an obesity due to the reduction of the muscle amount in the old age has been continuously increasing from 30% worldwide. Abnormal insulin secretion may cause a muscle development disorder due to poor energy supply to cells, such that sarcopenia increases in patients having diabetes mellitus compared to a normal person. In addition, a decrease in muscle causes more arthritis, back pain, chronic pain and causes urinary incontinence caused by abdominal obesity to be worsen. Fracture injuries may lead to increased depression in an old age, leading to death. Thus, sarcopenia in the old age is associated with various diseases and thus is a major cause of poor quality of life.

The sarcopenia refers to a condition in which the amount and function of a skeletal muscle are reduced. The sarcopenia is caused by a variety of causes, including aging, hormonal abnormalities, malnutrition, lack of physical activity, inflammatory and degenerative diseases. Among them, cancer, aging and sex hormone deficiency are known to be a major cause of the sarcopenia. Due to the development of medical technology and the development of various treatment agents, the aging population is increasing as life expectancy increases. Accordingly, the demand for treatment of sarcopenia is expected to increase continuously. In patients with sarcopenia, the number of myoblasts decreases due to disorder of gathering, activity or proliferation of satellite cells as stem cells of myoblasts, and a decrease in myoblast proliferation and differentiation occurs. As a result, the muscle of the patient having sarcopenia has a decrease in the size and number of muscular fibers at a histological level, leading to decreased muscle function. In the past decade, research on the epidemiology of sarcopenia has been actively conducted in the United States and Europe. Then, the interest in the clinical significance of sarcopenia has recently increased. Early studies have shown that sarcopenia causes poor quality of life due to systemic weakness, impaired activity and decreased muscle strength. Recent studies have reported that sarcopenia causes a significant increase in the risk of osteoporotic fractures in addition to the deterioration of the quality of life. Further, in sarcopenia patients, chronic diseases such as diabetes and metabolic syndrome, obesity, chronic renal failure, chronic liver failure, etc. are developed, leading to the increased mortality. Thus, sarcopenia is of interest as a disease that must be treated properly. Recently, it is reported in the United States that a 1.5 to 3.5-fold increase in the likelihood of developing physical disabilities in sarcopenia patients occurs, resulting in $ 18.5 billion in social costs per year. In Korea, according to the National Health and Nutrition Survey, the prevalence of sarcopenia is 42.0% for males and 42.7% for females over 60 years old. In particular, as Korea has the fastest aging rate in the world, it is certain that the sarcopenia will be a significant social problem in the future.

Cancer-induced sarcopenia is caused by malnutrition, lack of exercise and cytokines secreted by cancer such that muscle mass and physical function are significantly reduced. According to statistics, sarcopenia caused by cancer is found in 14 to 78.7% of all cancer patients. According to statistics, sarcopenia caused by cancer is found in more than 50% of patients of cancers of a digestive system and in about 40% of patients of lung cancer and liver cancer. According to a recent report from the European Cancer Center, patients with esophageal cancer having sarcopenia had an average of 2 years and 8 months of shortening of life expectancy and showed an increase in complications of cancer surgery compared to patients with esophageal cancer without sarcopenia. According to a Japanese cancer center report, the number of patients who survived without cancer reoccurrence for five years after liver cancer surgery is doubled in the absence of sarcopenia compared to the presence thereof. Thus, sarcopenia may affect the cancer recurrence. In patients with sarcopenia, anticancer drug discontinuation and dose reduction also occur more frequently than in patients without sarcopenia, Thus, the sarcopenia affects an overall survival percentage. Thus, sarcopenia may be a bad factor that greatly affects the overall survival of the cancer patients. There is a need for a solution for sarcopenia.

Sarcopenia caused by degeneration of spinal nerve, motor nerve or skeletal muscle fibers associated with muscle disease is one of representative refractory diseases for which a causing factor has not yet been identified. So far, research has shown that the motor nerves that induce skeletal muscle contraction degenerate such that contraction of the skeletal muscle does not progress, or the expression of proteins involved in muscle contraction in the skeletal muscle is reduced or the protein is modified so that normal skeletal muscle contraction does not proceed, and in the long term, the motor nerve or skeletal muscle is transformed into fibrous tissue. The underlying cause of sarcopenia has not yet been identified. No method has been developed to prevent motor neuron or skeletal muscle degeneration or recover the motor neuron or skeletal muscle. Thus, at present, studies are being actively conducted to develop a method for slowing the progress of sarcopenia. Currently, exercise, protein and calorie supplements are known to help with reduction of sarcopenia. For the elderly, who make up the majority of sarcopenia patients, the exercise, protein and calorie supplements are not very helpful. Thus, a treatment agent of sarcopenia is urgently required. However, for the drugs currently used for sarcopenia, a drug having a direct effect on reducing the muscle loss and increasing muscle mass is still at the stage of clinical experiments. Currently, no drug is finally approved by the FDA. There are efforts to develop, as a treatment agent of sarcopenia, selective androgen receptor modulators, activin receptor antagonists, and fast skeletal muscle troponin inhibitors to treat the sarcopenia. However, those are currently at the initial clinical trial. Currently, a method of treating sarcopenia includes a method of suppressing muscular atrophy caused by degeneration or progressive mutation of muscle cells, which is a kind of sarcopenia. For example, WO 2007/088123 discloses a therapeutic agent for muscular atrophy, which contains a nitrooxy derivative as an active ingredient. WO 2006/081997 discloses a therapeutic agent for muscular atrophy, which contains an atraric acid or a derivative thereof as an active ingredient. However, these therapeutic agents comprising compounds as active ingredients act not only on skeletal muscles in which muscular atrophy is developed, but also on visceral or myocardium that is not associated with muscular atrophy. Thus, various side effects may be caused. Thus, the above agents are not used for practical treatment. On the other hand, hormonal preparations have significantly lowered side effects than compound preparations and the hormonal preparations are bio-friendly. Thus, the development of drugs for treating muscular atrophy or sarcopenia using hormonal preparations is being accelerated.

According to reports on sarcopenia treatment trends, the global sarcopenia treatment market in 2010 amounted to approximately $ 10 million (US) and grows to $ 20 million in 2018 ("Sarcopenia Therapeutics-Pipeline Assessment and Market Forecasts to 2018", Nov. 17, 2011). Further, in 2013, the EU Innovative Meticines Initiative as a private custody partnership under the EU announced an ongoing investment of approximately 50 million euros for the development of the elderly sarcopenia treatment as one of the four major health research topics.

DISCLOSURE

Technical Problem

The present inventors have identified from finding preventive and therapeutic substances for muscular disease, that dimenhydrinate, harmol or calcium pantothenate has therapeutic effects on muscular disease, especially sarcopenia, and a combination thereof has a synergy effect. Thus, the present disclosure was completed.

Technical Solution

In order to achieve the above object, the present disclosure provides a pharmaceutical composition for prevention or treatment of a muscular disease, the composition comprising dimenhydrinate, harmol or calcium pantothenate as an active ingredient.

Further, the present disclosure provides a pharmaceutical composition for the prevention or treatment of muscle and fat loss due to administration of an anticancer drug, the composition comprising dimenhydrinate or calcium pantothenate as an active ingredient.

In addition, the present disclosure provides a food composition for prevention or amelioration of a muscular disease, the composition comprising dimenhydrinate, harmol or calcium pantothenate.

Advantageous Effects

Dimenhydrinate, harmol and calcium pantothenate in accordance with the present disclosure alone have an effect of promoting the proliferation and differentiation of myoblasts. In particular, the combination of these has an effect of synergistically increasing the proliferation and differentiation promoting effects of myoblast. Thus, the dimenhydrinate, harmol and calcium pantothenate may be usefully used for the prevention or treatment of the muscular disease alone or in combinations thereof. The dimenhydrinate, harmol and calcium pantothenate may also be used to prevent or treat the muscle and fat loss caused by anticancer drugs.

MODES OF THE INVENTION

Figure 1:
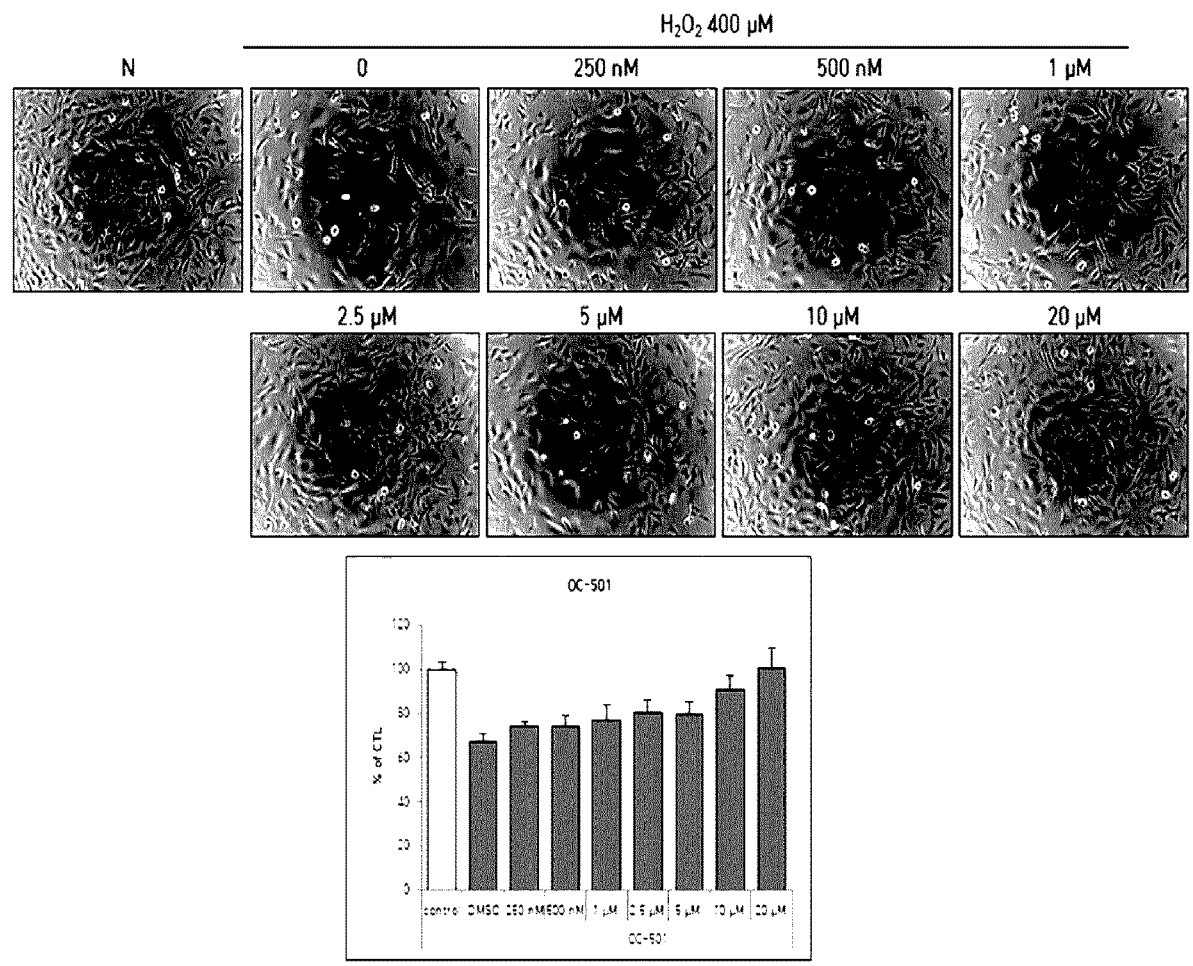
FIG. 1 is a photograph and graph showing the effect of promoting myoblast proliferation by dimenhydrinate (OC-501) application according to the present disclosure.

Hereinafter, exemplary embodiments of the present disclosure will be described in detail with reference to the accompanying drawings. However, the following embodiments are presented as an example of the present disclosure. When it is determined that the detailed description of the well-known technology or construction known to those skilled in the art may unnecessarily obscure the subject matter of the present disclosure, detailed descriptions thereof will be omitted. The present disclosure may be subjected to various modifications and applications within the scope of the following claims and their equivalents.

The terminology used herein is for the purpose of describing particular embodiments only and is not intended to be limiting of the present disclosure. This may vary depending on the intention of the user, the operator, or customs in the field to which the present invention belongs. Therefore, the definitions of the terms should be made based on the contents throughout the specification. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. Although described herein are preferred methods or samples, equivalent thereto are included in the category of the present disclosure. The contents of all publications incorporated herein by reference are incorporated into the present disclosure.

In one aspect, the present disclosure relates to a pharmaceutical composition for the prevention or treatment of muscular diseases, the composition comprising dimenhydrinate, harmol or calcium pantothenate as an active ingredient.

In one implementation, the dimenhydrinate may include a compound of molecular formula $C_{24}H_{28}ClN_5O_3$ and molecular weight 469.97 g/mol, as represented by a following Chemical Formula 1:

[Chemical Formula 1]

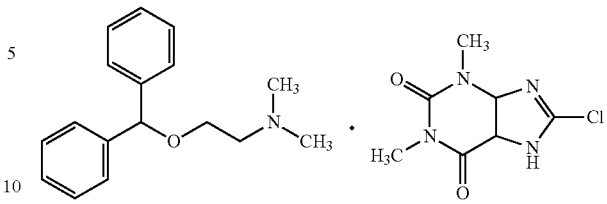

In one implementation, the harmol may include a compound of molecular formula $C_{12}H_{10}N_2O$ and a molecular weight of 198.225 g/mol as represented by a following Chemical Formula 2:

[Chemical Formula 2]

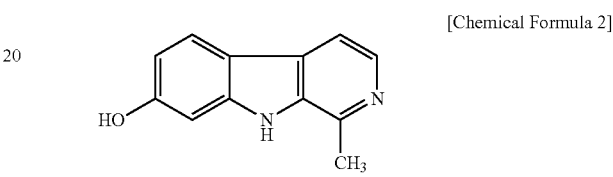

In one implementation, the calcium pantothenate may refer to a calcium salt of water-soluble vitamin B5, and may include a compound of molecular formula $C_{18}H_{32}CaN_2O_{10}$ and molecular weight 476.536 g/mol as represented by a following Chemical Formula 3:

[Chemical Formula 3]

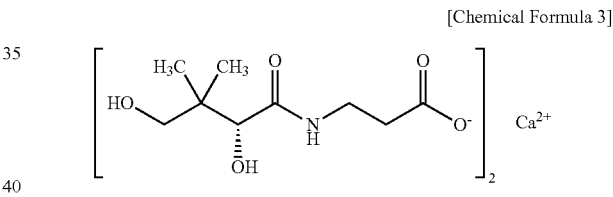

In one implementation, the calcium pantothenate may comprise vitamins. The vitamin may include a water-soluble vitamin selected from the group consisting of vitamin C, vitamin B1, vitamin B2, vitamin B6, vitamin H, vitamin PP or pro-vitamin B5 or mixtures thereof. The vitamin may include a fat-soluble vitamin selected from the group consisting of vitamin A, vitamin D, vitamin E, vitamin K1 or carotene or mixtures thereof. In a more preferred example, the vitamin may include vitamin B2 (riboflavin, vit B2).

In one implementation, each of dimenhydrinate, harmol and calcium pantothenate may be contained in a content range of from 250 nM to 20 μM. More preferably, the harmol may be contained in a content range of 500 nM to 10 μM and the calcium pantothenate may be contained in a content range of 500 nM to 20 μM.

In one implementation, the pharmaceutical composition according to the present disclosure may contain a combination of dimenhydrinate and harmol, a combination of dimenhydrinate and calcium pantothenate, a combination of harmol and calcium pantothenate, or a combination of dimenhydrinate, harmol and calcium pantothenate as an active ingredient. In one example, the pharmaceutical composition according to the present disclosure may contain combinations of dimenhydrinate, harmol and/or calcium pantothenate as follows: dimenhydrinate 5 μM+harmol 250 nM, dimenhydrinate 5 μM+harmol 500 nM, dimenhydrinate 5 μM+calcium pantothenate 5 μM, dimenhydrinate 5 μM+calcium pantothenate 10 μM, dimenhydrinate 10 μM+harmol 250 nM, dimenhydrinate 10 μM+harmol 500 nM, dimenhydrinate 10 μM+calcium pantothenate 5 μM, dimenhydrinate 10 μM+calcium pantothenate 10 μM, harmol 250 nM+calcium pantothenate 5 μM, harmol 250 nM+calcium pantothenate 10 μM, harmol 500 nM+calcium pantothenate 5 μM, harmol 500 nM+calcium pantothenate 10 μM, dimenhydrinate 5 μM+harmol 250 nM+calcium pantothenate 5 μM, dimenhydrinate 5 μM+harmol 250 nM+calcium pantothenate 10 μM, dimenhydrinate 10 μM+harmol 250 nM+calcium pantothenate 5 μM, dimenhydrinate 10 μM+harmol 250 nM+calcium pantothenate 10 μM, dimenhydrinate 5 μM+harmol 500 nM+calcium pantothenate 5 μM, dimenhydrinate 5 μM+harmol 500 nM+calcium pantothenate 10 μM, dimenhydrinate 10 μM+harmol 500 nM+calcium pantothenate 5 μM, and dimenhydrinate 10 μM+harmol 500 nM+calcium pantothenate 10 μM. In a preferable example, the pharmaceutical composition according to the present disclosure may contain combinations of dimenhydrinate, harmol and/or calcium pantothenate as follows: dimenhydrinate 10 μM+calcium pantothenate 5 μM, dimenhydrinate 10 μM+calcium pantothenate 10 μM, harmol 250 nM+calcium pantothenate 5 μM, and harmol 250 nM+calcium pantothenate 10 μM.

In one implementation, the muscular disease may include a muscular disease due to muscular dysfunction, muscle loss or muscle degeneration and may include one or more selected from a group consisting of atony, muscular atrophy, muscular dystrophy, myasthenia, cachexia and sarcopenia. More preferably, the muscular disease may include sarcopenia due to aging or cancer.

In one implementation, dimenhydrinate, harmol and/or calcium pantothenate in accordance with the present disclosure may increase muscle mass or muscle strength or improve muscle function via the promotion of myoblast proliferation and differentiation.

In one implementation, dimenhydrinate, harmol and/or calcium pantothenate in accordance with the present disclosure may prevent or treat muscle or fat loss due to anticancer treatment.

In one implementation, the anticancer treatment may involve in one or more selected from a group consisting of anticancer agents, chemotherapeutic agents, immunotherapy agents, antibacterial agents, radiotherapy agents and antiviral agents, and photodynamic therapy. The anticancer agent may be 5-FU (5-fluorouracil).

The composition in accordance with the present disclosure contains not only dimenhydrinate, harmol and calcium pantothenate represented by the Chemical Formulas 1 to 3, but also pharmaceutically acceptable salts thereof, and possible solvates, hydrates, racemates or stereoisomers that may be prepared therefrom.

Dimenhydrinate, harmol and calcium pantothenate as represented by Chemical Formulas 1 to 3 according to the present disclosure may be used in the form of pharmaceutically acceptable salts. The salts may be acid addition salts formed with pharmaceutically acceptable free acids. Acid addition salts may include inorganic acids such as hydrochloric acid, nitric acid, phosphoric acid, sulfuric acid, hydrobromic acid, hydroiodic acid, nitrous acid or phosphorous acid, non-toxic organic acids such as aliphatic mono and dicarboxylates, phenyl-substituted alkanoates, hydroxy alkanoates and alkanedioates, aromatic acids, aliphatic and aromatic sulfonic acids. Such pharmaceutically non-toxic salts may include sulfate, pyrosulfate, bisulfate, sulfite, bisulfite, nitrate, phosphate, monohydrogen phosphate, diaidogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butine-1,4-dioate, hexane-1,6-dioate, benzoate, chlorobenzoate, methylbenzoate, dinitro benzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, hydroxybutyrate, glycolate, malate, tartrate, methanesulfonate, propanesulfonate, naphthalene-1-sulfonate, naphthalene-2-sulfonate or mandelate.

Acid addition salts according to the present disclosure may be prepared by conventional methods, for example, by dissolving dimenhydrinate, harmol and calcium pantothenate as represented by Chemical Formulas 1 to 3 in an excess of aqueous solution of acid, and by precipitation of the salts with a water-miscible organic solvent such as methanol, ethanol, acetone or acetonitrile. Further, the acid addition salts according to the present disclosure may be prepared by evaporation of solvents or excess acid from the mixture and drying the mixture, or by absorbing-filtration of the precipitated salts.

Further, bases may be used to produce the pharmaceutically acceptable metal salts. Alkali metal or alkaline earth metal salts may be prepared, for example, by dissolving the compound in an excess of alkali metal hydroxide or alkaline earth metal hydroxide solution, and filtering non-dissolved compound salts, and evaporating and drying the filtrate. In this case, it is pharmaceutically suitable to prepare sodium, potassium or calcium salts as the metal salt. Further, the corresponding silver salt may be obtained by reacting an alkali or alkaline earth metal salt with a suitable silver salt (e.g. silver nitrate).

The pharmaceutical composition according to the present disclosure may further contain known muscular disease therapeutic agents in addition to dimenhydrinate, harmol and calcium pantothenate as active ingredients. The pharmaceutical composition according to the present disclosure may be combined with other treatment agents known for the treatment of the muscular diseases.

In one aspect, the present disclosure relates to a pharmaceutical composition for the prevention or treatment of muscle and fat loss caused by anticancer drugs, the composition comprising dimenhydrinate or calcium pantothenate as an active ingredient.

As used herein, the term "prevention" means any action that inhibits or delays the occurrence, spread and recurrence of the muscular disease by administration of the pharmaceutical composition according to the present disclosure. As used herein, the term "treatment" means any action that reduces or beneficially alters the symptoms of the muscular disease by administration of one or more selected from the group consisting of dimenhydrinate, harmol, and calcium pantothenate, or a pharmaceutically acceptable salt thereof, or a composition comprising the same according to the present disclosure. The person having ordinary knowledge in the technical field to which the present disclosure belongs refers to the materials presented by the Korean Medical Association, etc. to determine the exact criteria of the disease on which the composition according to the present disclosure will act effectively and to determine the extent of reduction, improvement and treatment thereof.

As used herein, the term "therapeutically effective amount" as used in combination with an active ingredient means an amount effective to prevent or treat a subject disease. The therapeutically effective amount of the composition according to the present disclosure may vary depending on several factors, such as the method of administration, the site of destination, and the condition of the patient. Therefore, when used in humans, the dosage should be determined in an appropriate amount in consideration of both safety and efficiency. It is possible to estimate the amount used in humans from the effective amount determined from the animal testing. Considerations in determining the effective amount are described, for example, in a following document: Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The pharmaceutical composition according to the present disclosure is administered in a pharmaceutically effective amount. As used herein, the term "pharmaceutically effective amount" means an amount sufficient to treat the disease that does not cause side effects at a reasonable benefit/risk ratio applicable to medical treatment. The effective dose level may be determined based on the patient's condition, the type of muscular disease, the cause of the muscular disease, the severity, the activity of the drug, the sensitivity to the drug, the method of administration, the time of administration, the route of administration and the rate of release, duration of treatment, drugs for combination or concurrent use, or other factors well known in the medical arts. The composition according to the present disclosure may be administered as an individual therapeutic agent or in combination with other therapeutic agents and may be administered sequentially or simultaneously with a conventional therapeutic agent and may be administered in a single dose or multiple doses. It is important to administer an amount that will achieve the maximum effect with a minimum amount without side effects, with taking all of the above factors into consideration. The amount may be readily determined by one skilled in the art.

The pharmaceutical compositions according to the present disclosure may comprise carriers, diluents, excipients or combinations of two or more commonly used in biological products. As used herein, the term "pharmaceutically acceptable" refers to being non-toxic to cells or humans exposed to the composition. The carrier is not particularly limited as long as the carrier is suitable for in vivo delivery of the composition. For example, the carrier may employ a compound recited in Merck Index, 13th ed., Merck & Co. Inc., saline solution, sterile water, Ringer's solution, buffered saline solution, dextrose solution, maltodextrin solution, glycerol, ethanol and a mixture of at least two of these components. If desired, other conventional additives such as antioxidants, buffers, fungistats, and the like may be added to the composition. Further, diluents, dispersants, surfactants, binders and lubricants may be additionally added to the composition to formulate the composition into injectable formulations, such as aqueous solutions, suspensions, emulsions and the like, pills, capsules, granules or tablets. Furthermore, the composition may be preferably formulated based on each disease or component using a suitable method in the art or using a method disclosed in Remington's Pharmaceutical Science (Mack Publishing Company, Easton Pa., 18th, 1990).

In one implementation, the pharmaceutical composition may be prepared in one or more formulations selected from the group consisting of oral formulations, external application preparations, suppositories, sterile injectable solutions and sprays. In a more preferred example, the pharmaceutical composition may be prepared in oral or injectable formulations.

As used herein, the term "administration" means provision of a predetermined substance to an individual or patient in any suitable way. Depending on the method as desired, the substance may be administered non-orally (for example, applied as an injectable formulation intravenously, subcutaneously, intraperitoneally or topically) or orally. Dosage may vary according to the patient's weight, age, sex, health condition, diet, time of administration, method of administration, rate of excretion and severity of disease. Liquid preparations for oral administration of the composition according to the present disclosure include suspensions, solutions, emulsions, and syrups. Various excipients, such as wetting agents, sweeteners, fragrances, preservatives, etc., in addition to the commonly used simple diluents, water and liquid paraffin may be contained in the composition. Preparations for parenteral administration include sterile aqueous solutions, non-aqueous solvents, suspensions, emulsions, lyophilized preparations, suppositories, and the like. The pharmaceutical composition according to the present disclosure may be administered by any device that allows the active substance to migrate to the target cell. Preferred modes of administration and preparations may include intravenous, subcutaneous, intradermal, intramuscular, drip injectables and the like. The injectables may be prepared using aqueous solvents such as physiological saline solution and ringers solution, vegetable oils, higher fatty acid esters (e.g., ethyl oleate, etc.), non-aqueous solvents such as alcohols (e.g., ethanol, benzyl alcohol, propylene glycol, glycerin, etc.). The injectables may contain stabilizers to prevent alteration (e.g. ascorbic acid, sodium bisulfite, sodium pyrosulfite, BHA, tocopherol, EDTA, etc.), emulsifiers, a pharmaceutical carrier such as a buffer for adjusting pH, a preservative for inhibiting microbial growth (e.g., phenyl mercury nitrate, thiomersal, benzalkonium chloride, phenol, cresol, benzyl alcohol, etc.).

As used herein, the term "individual" means all animals including monkeys, cows, horses, sheep, humans, pigs, chickens, turkeys, quails, cats, dogs, mice, rats, rabbits or guinea pigs that have or may have the muscular disease. Administering the pharmaceutical composition according to the present disclosure to the individual may allow the diseases to be effectively prevented or treated. The pharmaceutical composition according to the present disclosure may be administered in combination with existing therapeutic agents.

The pharmaceutical compositions according to the present disclosure may comprise further pharmaceutically acceptable additives. The pharmaceutically acceptable additives may include starch, gelatinized starch, microcrystalline cellulose, lactose, povidone, colloidal silicon dioxide, calcium hydrogen phosphate, lactose, mannitol, malt, arabian rubber, pregelatinized starch, corn starch, powdered cellulose, hydroxypropyl cellulose, Opadry, sodium starch glycolate, carnauba lead, synthetic aluminum silicate, stearic acid, magnesium stearate, aluminum stearate, calcium stearate, sucrose, dextrose, sorbitol, talc and the like. The pharmaceutically acceptable additive according to the present disclosure may be preferably contained in a range of 0.1 parts by weight to 90 parts by weight with respect to a weight of the composition but is not limited thereto.

In one aspect, the present disclosure relates to a pharmaceutical composition for the prevention or treatment of muscle and fat loss caused by anticancer drugs, the composition ddining dimenhydrinate or calcium pantothenate as active ingredients.

In one implementation, calcium pantothenate may comprise vitamins. The vitamin may include a water-soluble vitamin selected from the group consisting of vitamin C, vitamin B1, vitamin B2, vitamin B6, vitamin H, vitamin PP or pro-vitamin B5 or mixtures thereof. The vitamin may include a fat-soluble vitamin selected from the group consisting of vitamin A, vitamin D, vitamin E, vitamin K1 or carotene or mixtures thereof. In a more preferred example, the vitamin may include vitamin B2 (riboflavin, vit B2).

In one aspect, the present disclosure relates to a food composition for prevention or amelioration of a muscular disease, the composition comprising dimenhydrinate, harmol or calcium pantothenate.

In one implementation, calcium pantothenate may comprise vitamins. The vitamin may include a water-soluble vitamin selected from the group consisting of vitamin C, vitamin B1, vitamin B2, vitamin B6, vitamin H, vitamin PP or pro-vitamin B5 or mixtures thereof. The vitamin may include a fat-soluble vitamin selected from the group consisting of vitamin A, vitamin D, vitamin E, vitamin K1 or carotene or mixtures thereof. In a more preferred example, the vitamin may include vitamin B2 (riboflavin, vit B2).

In one implementation, each of dimenhydrinate, harmol and calcium pantothenate may be contained in a content range of from 250 nM to 20 µM. More preferably, the harmol may be contained in a content range of 500 nM to 10 µM and calcium pantothenate may be contained in a content range of 500 nM to 20 µM.

In one implementation, the pharmaceutical composition according to the present disclosure may comprise a combination of dimenhydrinate and harmol, a combination of dimenhydrinate and calcium pantothenate, a combination of harmol and calcium pantothenate, or a combination of dimenhydrinate, harmol and calcium pantothenate as an active ingredient. In one example, the pharmaceutical composition according to the present disclosure may comprise combinations of dimenhydrinate, harmol and/or calcium pantothenate as follows: dimenhydrinate 5 µM+harmol 250 nM, dimenhydrinate 5 µM+harmol 500 nM, dimenhydrinate 5 µM+calcium pantothenate 5 µM, dimenhydrinate 5 µM+calcium pantothenate 10 µM, dimenhydrinate 10 µM+harmol 250 nM, dimenhydrinate 10 µM+harmol 500 nM, dimenhydrinate 10 µM+calcium pantothenate 5 µM, dimenhydrinate 10 µM+calcium pantothenate 10 µM, harmol 250 nM+calcium pantothenate 5 µM, harmol 250 nM+calcium pantothenate 10 µM, harmol 500 nM+calcium pantothenate 5 µM, harmol 500 nM+calcium pantothenate 10 µM, dimenhydrinate 5 µM+harmol 250 nM+calcium pantothenate 5 µM, dimenhydrinate 5 µM+harmol 250 nM+calcium pantothenate 10 µM, dimenhydrinate 10 µM+harmol 250 nM+calcium pantothenate 5 µM, dimenhydrinate 10 µM+harmol 250 nM+calcium pantothenate 10 µM, dimenhydrinate 5 µM+harmol 500 nM+calcium pantothenate 5 µM, dimenhydrinate 5 µM+harmol 500 nM+calcium pantothenate 10 µM, dimenhydrinate 10 µM+harmol 500 nM+calcium pantothenate 5 µM, and dimenhydrinate 10 µM+harmol 500 nM+calcium pantothenate 10 µM. In a preferable example, the pharmaceutical composition according to the present disclosure may comprise combinations of dimenhydrinate, harmol and/or calcium pantothenate as follows: dimenhydrinate 10 µM+calcium pantothenate 5 µM, dimenhydrinate 10 µM+calcium pantothenate 10 µM, harmol 250 nM+calcium pantothenate 5 µM, and harmol 250 nM+calcium pantothenate 10 µM. In one embodiment, dimenhydrinate, harmol and calcium pantothenate according to the present disclosure showed a synergistic effect when they are contained in the composition in a combination manner rather than contained therein alone.

In one implementation, dimenhydrinate, harmol and/or calcium pantothenate in accordance with the present disclosure may increase muscle mass or muscle strength via the promotion of myoblast proliferation and differentiation.

In one implementation, the muscular disease may include a muscular disease due to muscular dysfunction, muscle loss or muscle degeneration and may include one or more selected from a group consisting of atony, muscular atrophy, muscular dystrophy, myasthenia, cachexia and sarcopenia. More preferably, the muscular disease may include sarcopenia due to aging or cancer.

When using the composition according to the present disclosure as a food composition, the dimenhydrinate, harmol or calcium pantothenate may be added as it is or may be used with other foods or food ingredients and may be used suitably according to a conventional method. The composition may comprise food-acceptable food supplement additives in addition to the active ingredient. The mixed amount of the active ingredient may be appropriately determined depending on the purpose of use (prevention, health or therapeutic treatment).

As used herein, the term "food supplement additive" means a component that may be added to a food in a supplementing manner and may be added to prepare the health functional food of each formulation and may be selected by those skilled in the art as appropriate. Examples of the food supplement additives may include flavors such as various nutrients, vitamins, minerals (electrolytes), synthetic and natural flavors, colorants and fillers, pectic acid and salts thereof, alginic acid and salts thereof, organic acids, protective colloidal thickeners, pH adjusters, stabilizers, preservatives, glycerin, alcohols, carbonation agents used in carbonated drinks. The examples above do not limit the type of the food supplement additive according to the present disclosure.

A health functional food may comprise the food composition according to the present disclosure. The term "health functional food" as used in the present disclosure refers to food products prepared and processed in the form of tablets, capsules, powders, granules, liquids, and pills using raw materials or ingredients having useful functions for the human body. Herein, the term 'functional' means to obtain a useful effect for health purposes such as nutrient control or physiological action on the structure and function of the human body. Health functional foods according to the present disclosure may be prepared by methods commonly used in the art. In the preparation, the food may be prepared by adding the raw materials and components commonly added in the art. In addition, the formulation of the health functional food may be prepared without limitation as long as the formulation is recognized as a health functional food. The food according to the present disclosure may be prepared in various forms of formulation. The food has the advantage that unlike a general medicine, there is no side effect that may occur when taking the medicine for a long time. Due to its high portability, health functional foods in accordance with the present disclosure may be taken as supplements to enhance the effectiveness of anticancer drugs.

Further, there is no limit to the type of the health functional foods in which the composition according to the present disclosure may be contained. In addition, a composition comprising the dimenhydrinate, harmol or calcium pantothenate as an active ingredient according to the present disclosure may be mixed with other appropriate additives and other known additives that may be included in the health functional food according to the choice of those skilled in the art. Examples of the foods may include meat, sausages, bread, chocolate, candy, snacks, confectionery, pizza, ramen, other noodles, gum, dairy products comprising ice cream, various soups, beverages, tea, drinks, alcoholic drinks and vitamin complexes. The food may be prepared by adding the composition according to the present disclosure as a main ingredient into tea, jelly and juice.

[Beat Mode]

The present disclosure is explained in more detail based on the following example. However, the following example is intended to embody the present disclosure, and thereby does not limit the present disclosure.

EXAMPLE 1

Identifying Effect of Application of Single Component 1-1. Identifying Effect of Dimenhydrinate Application 1-1-1. Identifying Promoting Effect of Myoblast Proliferation by Dimenhydrinate Application Mouse myoblast strain C2C12 was dispensed in 96-well plates at $1.5 \times 10^3$ cells/well, and then cultured in DMEM medium containing 10% fetal bovine serum (FBS) at 37° C. and 5% $CO_2$ for one day at a low density manner. Thereafter, the medium was replaced with DMEM medium containing 400 nM $H_2O_2$ and 0 nM, 250 nM, 500 nM, 1 μM, 2.5 μM, 5 μM, 10 μM or 20 μM of dimenhydrinate (OC-501) respectively. At 16 hours since the replacement, the wells were treated with MTT reagent and then the mouse myoblast strain C2C12 was incubated in the DMEM medium in a dark incubator for 3 hours. After removing supernatant therefrom and applying 100 μl of DMSO to the well, the optical density (OD) was measured at 595 nm. Cells were identified using a microscope.

As a result, dimenhydrinate was found to promote myoblast proliferation (FIG. 1).

1-1-2. Identifying Promoting Effects of Myoblast Differentiation by Dimenhydrinate Application Mouse myoblast strain C2C12 was dispensed into 12-well plates at $0.7 \times 10^5$ cells/well and then cultured to a cell density of 70 to 80%. The cells were then washed with PBS and then the medium was replaced with DMEM medium (differentiation medium) containing 2% horse serum, 400 μM $H_2O_2$, and dimenhydrinate (OC-501) of 0 nM (DMSO), 500 nM, 5 μM, 10 μM or 20 μM respectively. Differentiation of the myoblast was induced for 5 to 7 days while the replacement of the medium occurred every other day. After the differentiation, cells were identified using a microscope (4× and 10× magnification), and cells were disrupted and then Western blot analysis was performed using differentiation markers myogenin and myosin heavy chain (MHC) antibodies.

Figure 2:
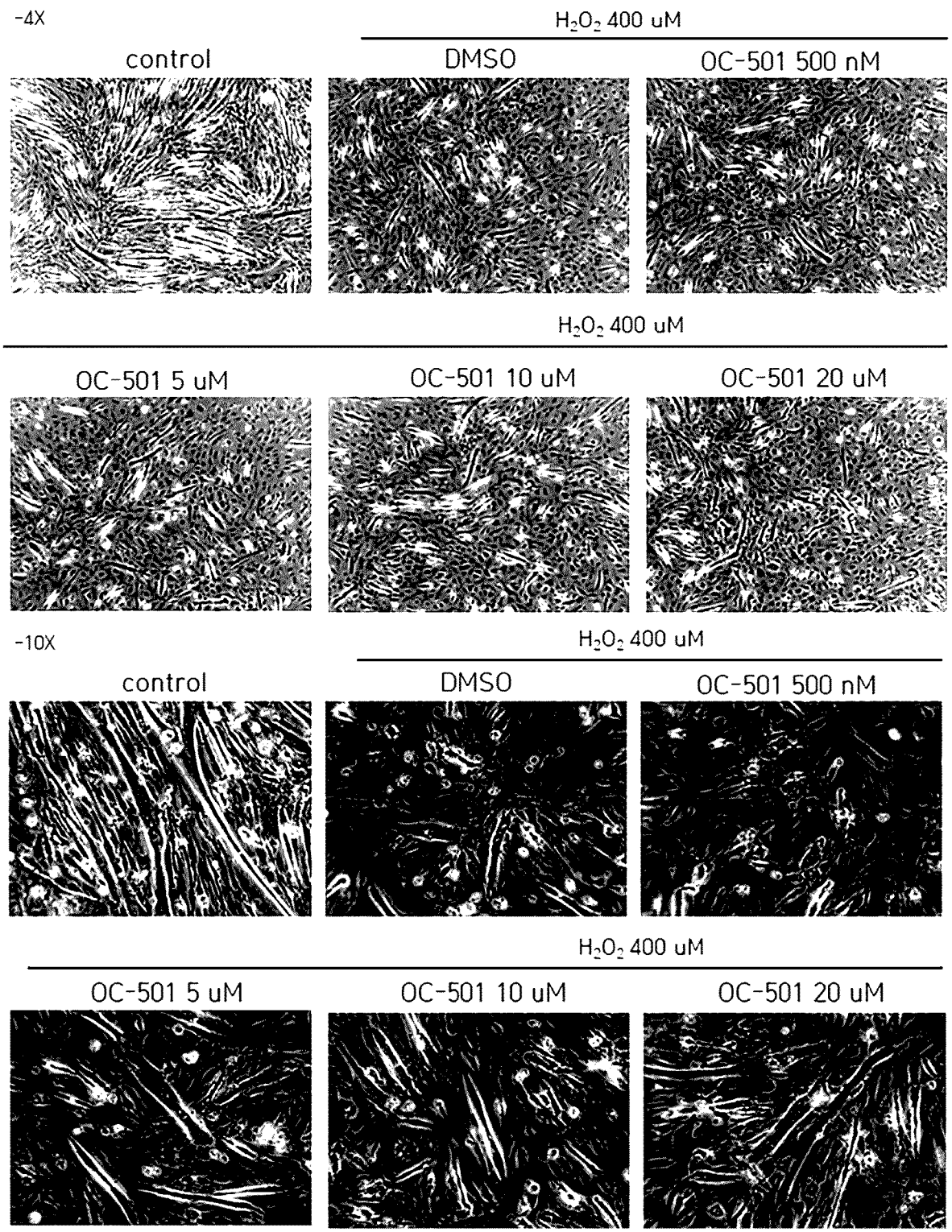
FIG. 2 is photographs identifying the differentiation-promoting effects of myoblasts by dimenhydrinate applications according to the present disclosure:
Upper: 4× magnification image after differentiation; and
Lower: 10× magnification image after differentiation.
Figure 3:
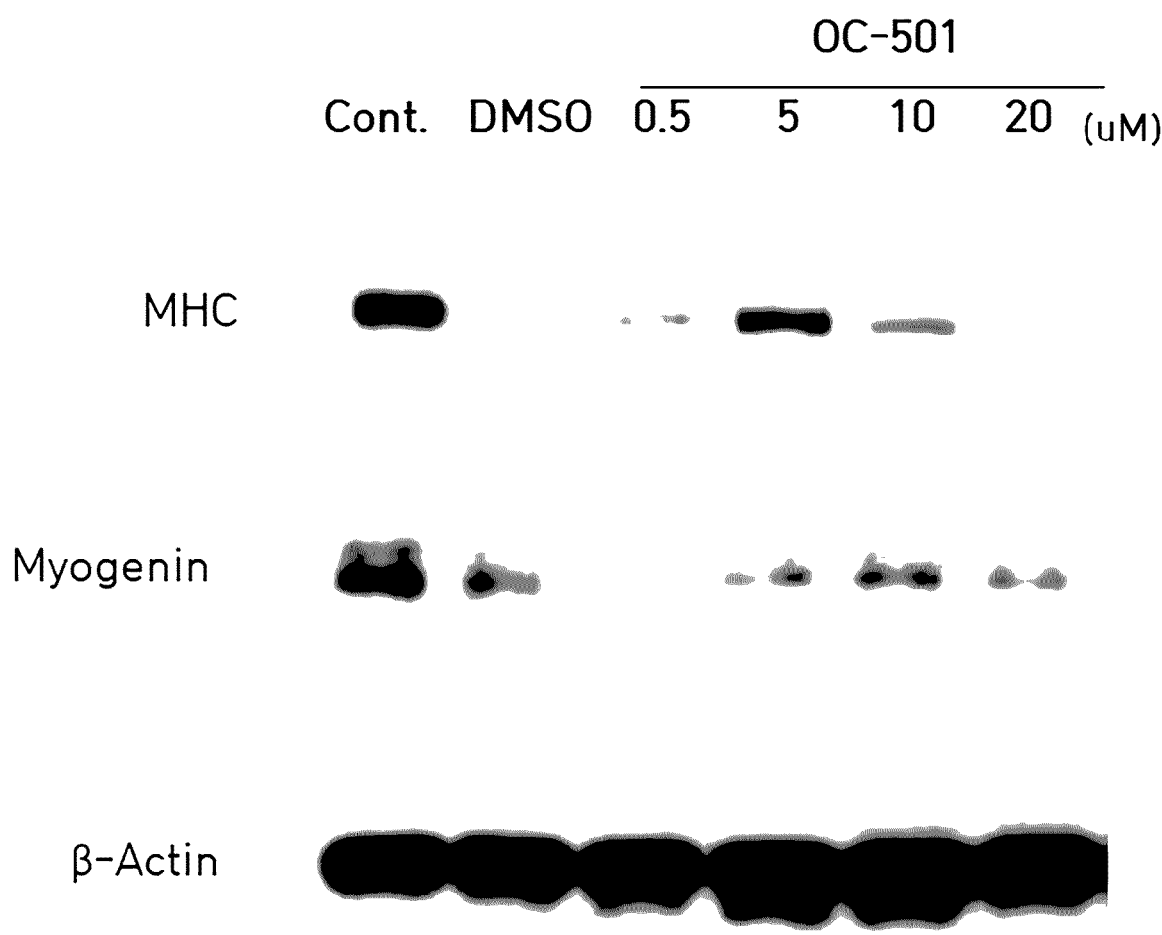
FIG. 3 shows a Western blot analysis of the expression level of muscle cell differentiation markers myogenin and MHC (myosin heavy chain).

As a result, dimenhydrinate promoted differentiation of myoblast (FIG. 2). The differentiation promotion increased especially at 5 μM of dimenhydrinate (FIG. 3).

1-2. Identifying Effect of Harmol Application 1-2-1. Identifying Promoting Effect of Myoblast Proliferation by Harmol Application Mouse myoblast strain C2C12 was dispensed in 96-well plates at $1.5 \times 10^3$ cells/well, and then cultured in DMEM medium containing 10% fetal bovine serum (FBS) at 37° C. and 5% $CO_2$ for one day at a low density manner. Thereafter, the medium was replaced with DMEM medium containing 400 nM $H_2O_2$ and 0 nM, 250 nM, 500 nM, 1 μM, 2.5 μM, 5 μM, 10 μM or 20 μM of harmol (OC-503) respectively. At 16 hours since the replacement, the wells were treated with MTT reagent and then the mouse myoblast strain C2C12 was incubated in the DMEM medium in a dark incubator for 3 hours. After removing supernatant therefrom and applying 100 μl of DMSO to the well, the optical density (OD) was measured at 595 nm. Cells were identified using a microscope.

Figure 4:
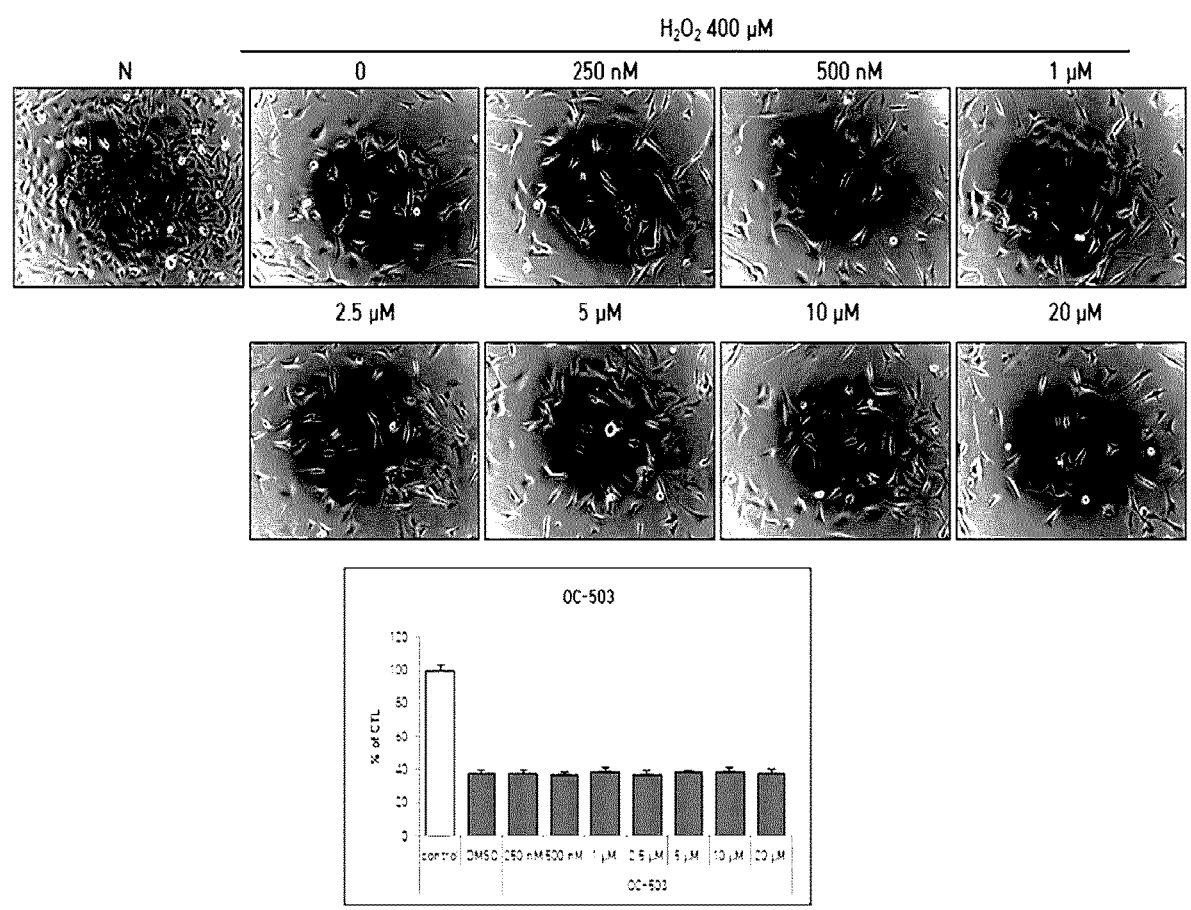
FIG. 4 is a photograph and graph showing the effect of promoting myoblast proliferation by harmol (OC-503) application according to the present disclosure.

As a result, harmol was found not to promote myoblast proliferation (FIG. 4).

1-2-2. Identifying Promoting Effects of Myoblast Differentiation by Harmol Application Mouse myoblast strain C2C12 was dispensed into 12-well plates at $0.7 \times 10^5$ cells/well and then cultured to a cell density of 70 to 80%. The cells were then washed with PBS and then the medium was replaced with DMEM medium (differentiation medium) containing 2% horse serum, 400 μM $H_2O_2$, and harmol (OC-503) of 0 nM (DMSO), 500 nM, 1 μM, 2.5 μM, 5 μM, or 10 μM respectively. Differentiation of the myoblast was induced for 5 to 7 days while the replacement of the medium occurred every other day. After the differentiation, cells were identified using a microscope, and cells were disrupted, and then Western blot analysis was performed using differentiation markers myogenin and myosin heavy chain (MHC) antibodies.

Figure 5:
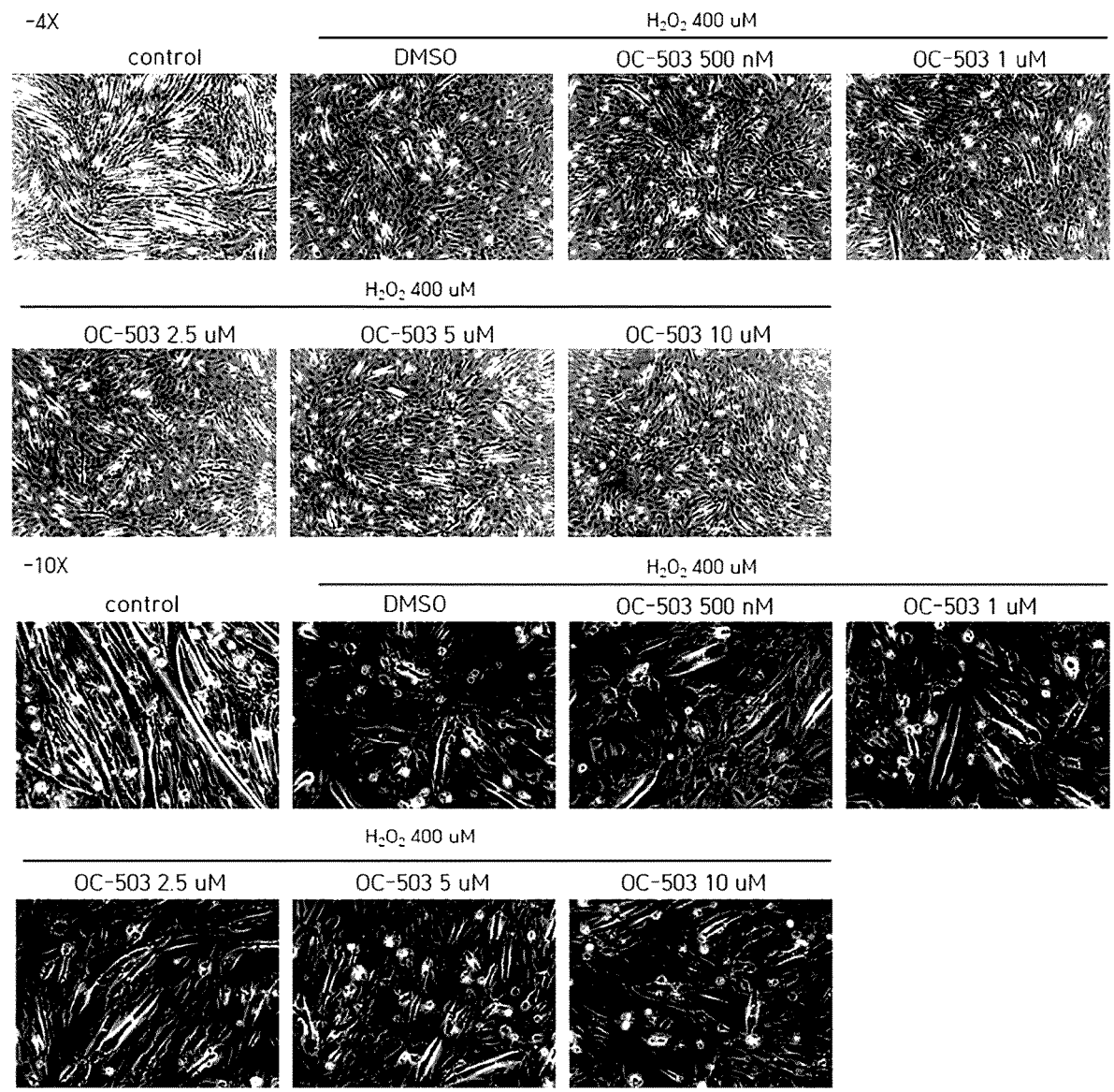
FIG. 5 is photographs showing the differentiation-promoting effects of myoblasts caused by the harmol application according to the present disclosure:
Upper: 4× magnification image after differentiation; and
Lower: 10× magnification image after differentiation.
Figure 6:
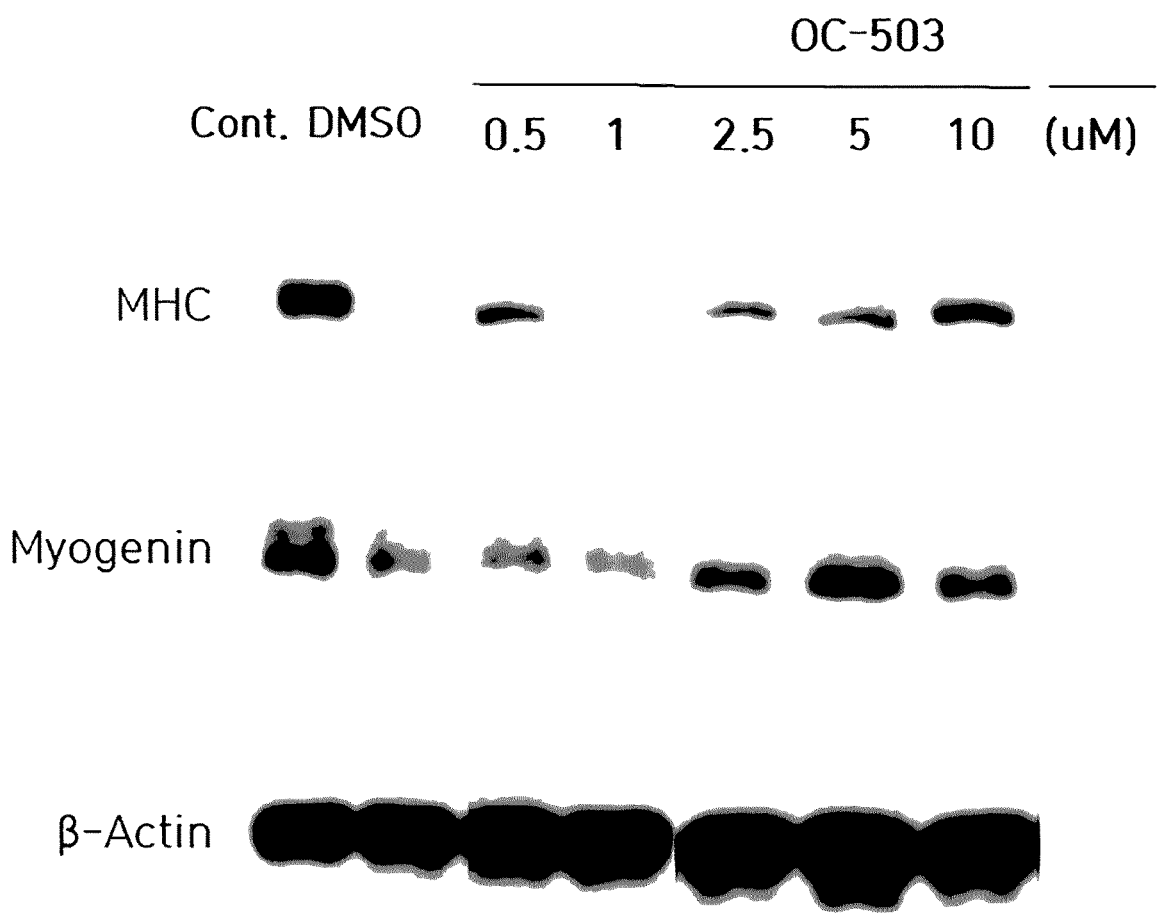
FIG. 6 shows the Western blot analysis of the expression levels of muscle cell differentiation markers myogenin and MHC (myosin heavy chain).

As a result, harmol promoted differentiation of myoblast (FIG. 5). The differentiation promotion increased especially at 5 μM and 10 μM of harmol (FIG. 6).

1-3. Identifying Effect of Calcium Pantothenate Application 1-3-1. Identifying Promoting Effects of Myoblast Proliferation by Calcium Pantothenate Application Mouse myoblast strain C2C12 was dispensed in 96-well plates at $1.5 \times 10^3$ cells/well, and then cultured in DMEM medium containing 10% fetal bovine serum (FBS) at 37° C. and 5% $CO_2$ for one day at a low density manner. Thereafter, the medium was replaced with DMEM medium containing 400 nM $H_2O_2$ and 0 nM, 250 nM, 500 nM, 1 μM, 2.5 μM, 5 μM, 10 μM or 20 μM of calcium pantothenate (OC-504) respectively. At 16 hours since the replacement, the wells were treated with MTT reagent and then the mouse myoblast strain C2C12 was incubated in the DMEM medium in a dark incubator for 3 hours. After removing supernatant therefrom and applying 100 μl of DMSO to the well, the optical density (OD) was measured at 595 nm. Cells were identified using a microscope.

Figure 7:
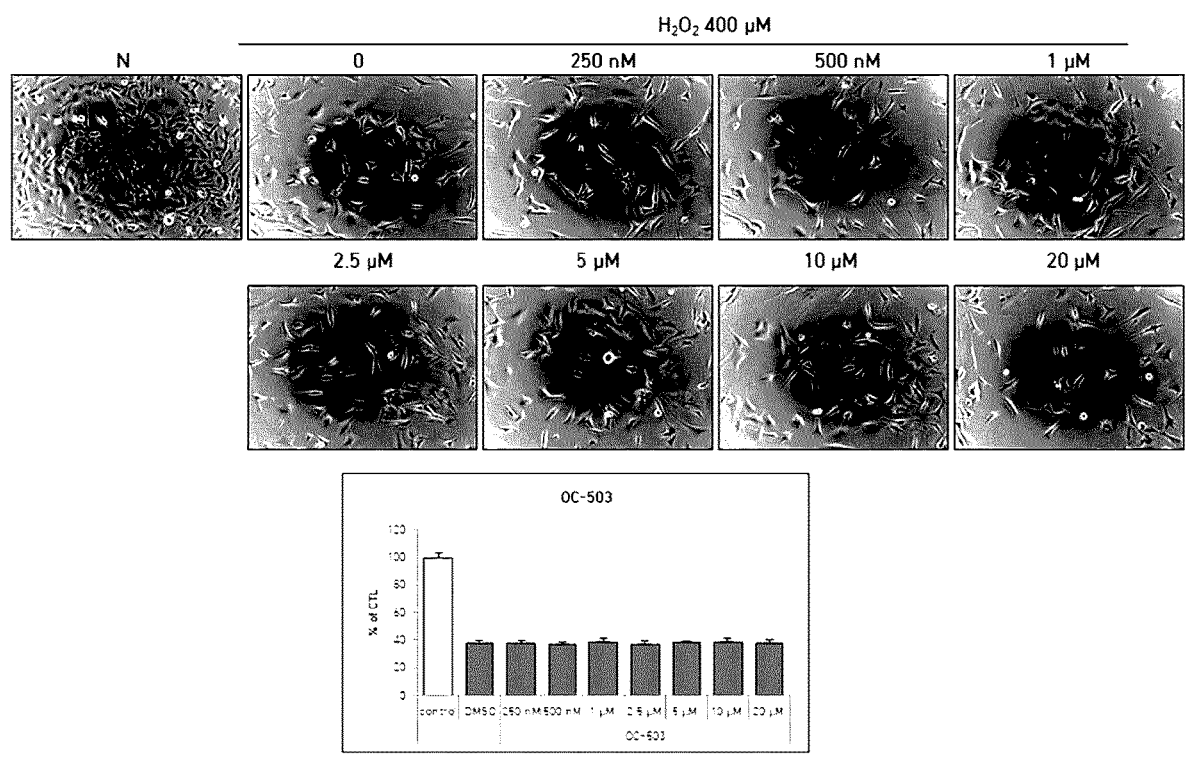
FIG. 7 is a photograph and graph showing the effect of promoting myoblast proliferation by calcium pantothenate (OC-504) application according to the present disclosure.

As a result, calcium pantothenate was found not to promote myoblast proliferation (FIG. 7).

1-3-2. Identifying Promoting Effects of Myoblast Differentiation by Calcium Pantothenate Application Mouse myoblast strain C2C12 was dispensed into 12-well plates at $0.7 \times 10^5$ cells/well and then cultured to a cell density of 70 to 80%. The cells were then washed with PBS and then the medium was replaced with DMEM medium (differentiation medium) containing 2% horse serum, 400 μM $H_2O_2$, and calcium pantothenate (OC-504) of 0 nM (DMSO), 500 nM, 2.5 μM, 5 μM, 10 μM or 20 μM respectively. Differentiation of the myoblast was induced for 5 to 7 days while the replacement of the medium occurred every other day. After the differentiation, cells were identified using a microscope (4× and 10× magnification), and cells were disrupted, and then Western blot analysis was performed using differentiation markers myogenin and myosin heavy chain (MHC) antibodies.

Figure 8:
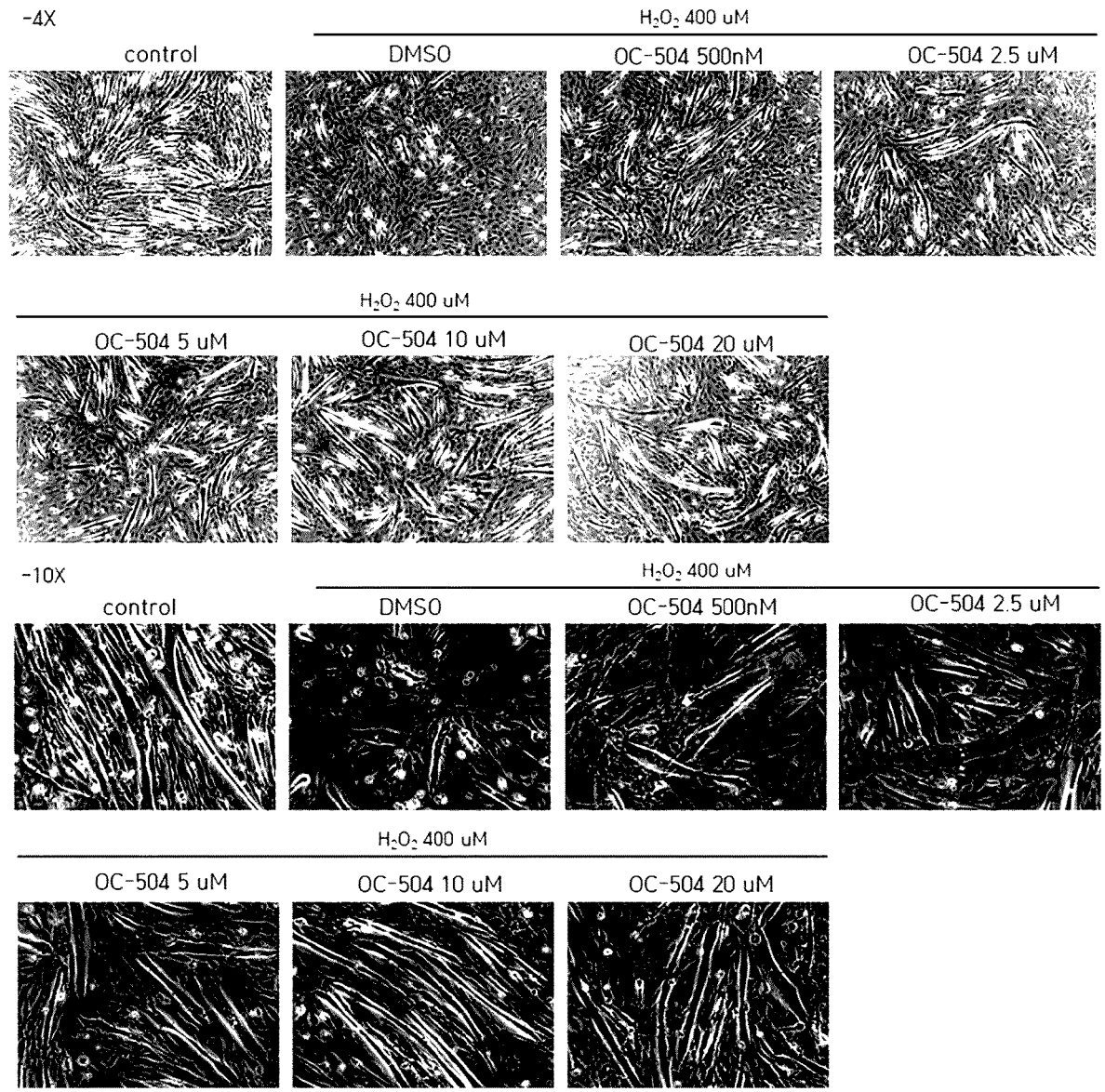
FIG. 8 is photographs identifying the differentiation-promoting effects of myoblasts by calcium pantothenate application according to the present disclosure:
Upper: 4× magnification image after differentiation; and
Lower: 10× magnification image after differentiation.
Figure 9:
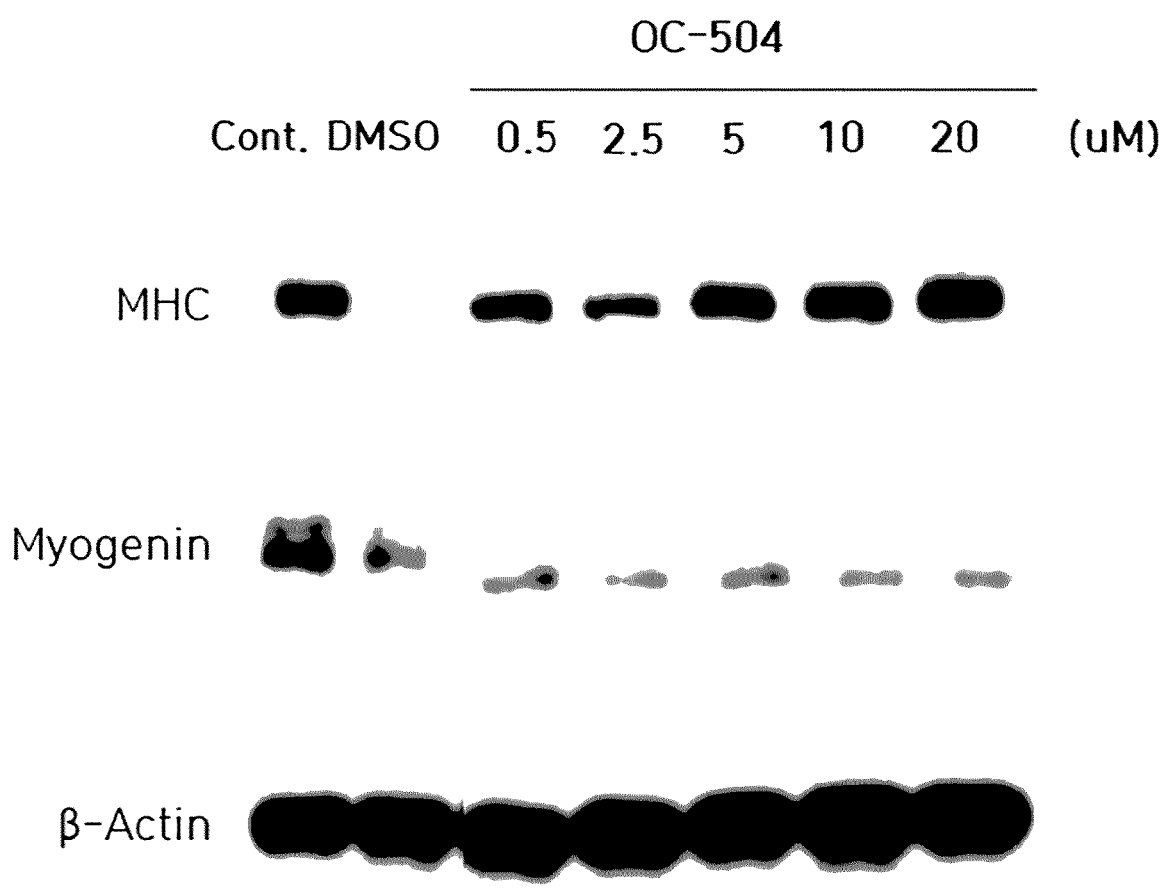
FIG. 9 shows the level of expression of muscle cell differentiation markers myogenin and MHC (myosin heavy chain) by Western blot analysis.

As a result, calcium pantothenate promoted differentiation of myoblast (FIG. 8). The differentiation promotion increased especially at 5 μM and 10 μM of calcium pantothenate (FIG. 9).

EXAMPLE 2

Identifying Effect of Application of Combination of Components 2-1. Cytotoxicity Identification Mouse myoblast strain C2C12 was dispensed in 96-well plates at $1.5 \times 10^3$ cells/well. A combination of dimenhydrinate (OC-501), harmol (OC-503) and calcium pantothenate (OC-504) was applied thereto. Then, the mouse myoblast strain C2C12 was cultured in DMEM medium containing 10% fetal bovine serum (FBS) and each of combinations of OC-501 5 μM+OC-503 250 nM, OC-501 5 μM+OC-503 500 nM, OC-501 5 μM+OC-504 5 μM, OC-501 5 μM+OC-504 10 μM, OC-501 10 μM+OC-503 250 nM, OC-501 10 μM+OC-503 500 nM, OC-501 10 μM+OC-504 5 μM, OC-501 10 μM+OC-504 10 μM, OC-503 250 nM+OC-504 5 μM, OC-503 250 nM+OC-504 10 μM, OC-503 500 nM+OC-504 5 μM, OC-503 500 μM+OC-504 10 μM, OC-501 5 μM+OC-503 250 nM+OC-504 5 μM, OC-501 5 μM+OC-503 250 nM+OC-504 10 μM, OC-501 10 μM+OC-503 250 nM+OC-504 5 μM, OC-501 10 μM+OC-503 250 nM+OC-504 10 μM, OC-501 5 μM+OC-503 500 nM+OC-504 5 μM, OC-501 5 μM+OC-503 500 nM+OC-504 10 μM, OC-501 10 μM+OC-503 500 nM+OC-504 5 μM, and OC-501 10 μM+OC-503 500 nM+OC-504 10 μM. At 24, 48, and 72 hours since the application, the wells were treated with MTT reagent and then the mouse myoblast strain C2C12 was incubated in the DMEM medium in a dark incubator for 3 hours. After removing supernatant therefrom and applying 100 μl of DMSO to each well, the optical density (OD) was measured at 595 nm to identify cytotoxicity. The experiment was performed three times.

Figure 10:
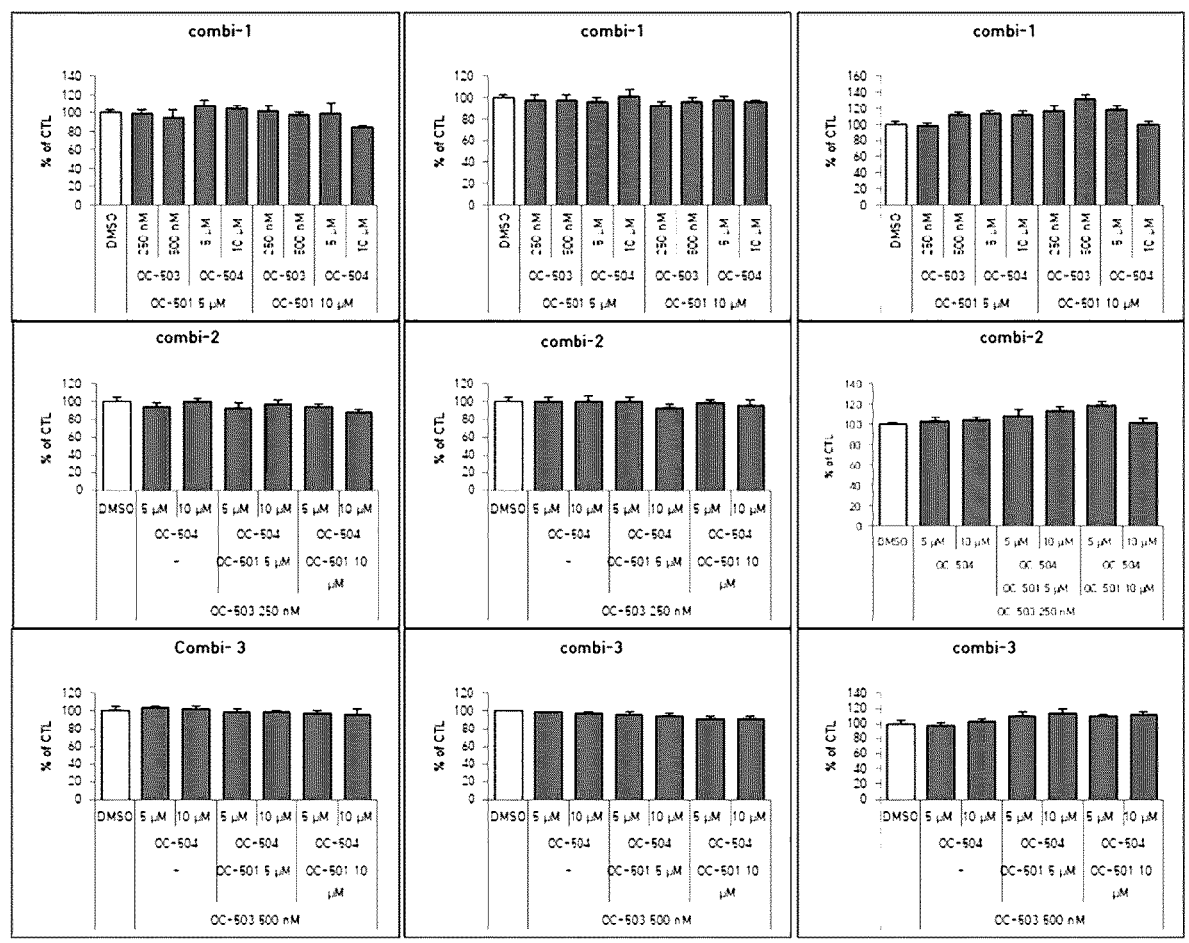
FIG. 10 shows the cytotoxicity to myoblasts when a combination of dimenhydrinate, harmol and calcium pantothenate is applied.

As a result, the combination of dimenhydrinate (OC-501), harmol (OC-503) and calcium pantothenate (OC-504) according to the present disclosure showed no cytotoxicity (FIG. 10).

2-2. Identifying Promoting Effects of Myoblast Differentiation by Combination Application Mouse myoblast strain C2C12 was dispensed in 96-well plates at $1.5 \times 10^3$ cells/well, and then cultured in DMEM medium containing 10% fetal bovine serum (FBS) at 37° C. and 5% $CO_2$ for one day at a low density manner. Thereafter, the medium was replaced with DMEM medium containing 400 μM $H_2O_2$ and each of following combinations of dimenhydrinate (OC-501), harmol (OC-503), and calcium pantothenate (OC-504): OC-501 5 μM+OC-503 250 nM, OC-501 5 μM+OC-503 500 nM, OC-501 5 μM+OC-504 5 μM, OC-501 5 μM+OC-504 10 μM, OC-501 10 μM+OC-503 250 nM, OC-501 10 μM+OC-503 500 nM, OC-501 10 μM+OC-504 5 μM, OC-501 10 μM+OC-504 10 μM, OC-503 250 nM+OC-504 5 μM, OC-503 250 nM+OC-504 10 μM, OC-503 500 nM+OC-504 5 μM, OC-503 500 nM+OC-504 10 μM, OC-501 5 μM+OC-503 250 nM+OC-504 5 μM, OC-501 5 μM+OC-503 250 nM+OC-504 10 μM, OC-501 10 μM+OC-503 250 nM+OC-504 5 μM, OC-501 10 μM+OC-503 250 nM+OC-504 10 μM, OC-501 5 μM+OC-503 500 nM+OC-504 5 μM, OC-501 5 μM+OC-503 500 nM+OC-504 10 μM, and OC-501 10 μM+OC-503 500 nM+OC-504 10 μM. At 16 hours since the replacement, the wells were treated with MTT reagent and then the mouse myoblast strain C2C12 was incubated in the DMEM medium in a dark incubator for 3 hours. After removing supernatant therefrom and applying 100 μl of DMSO to the well, the optical density (OD) was measured at 595 nm. Cells were identified using a microscope.

Figure 11:
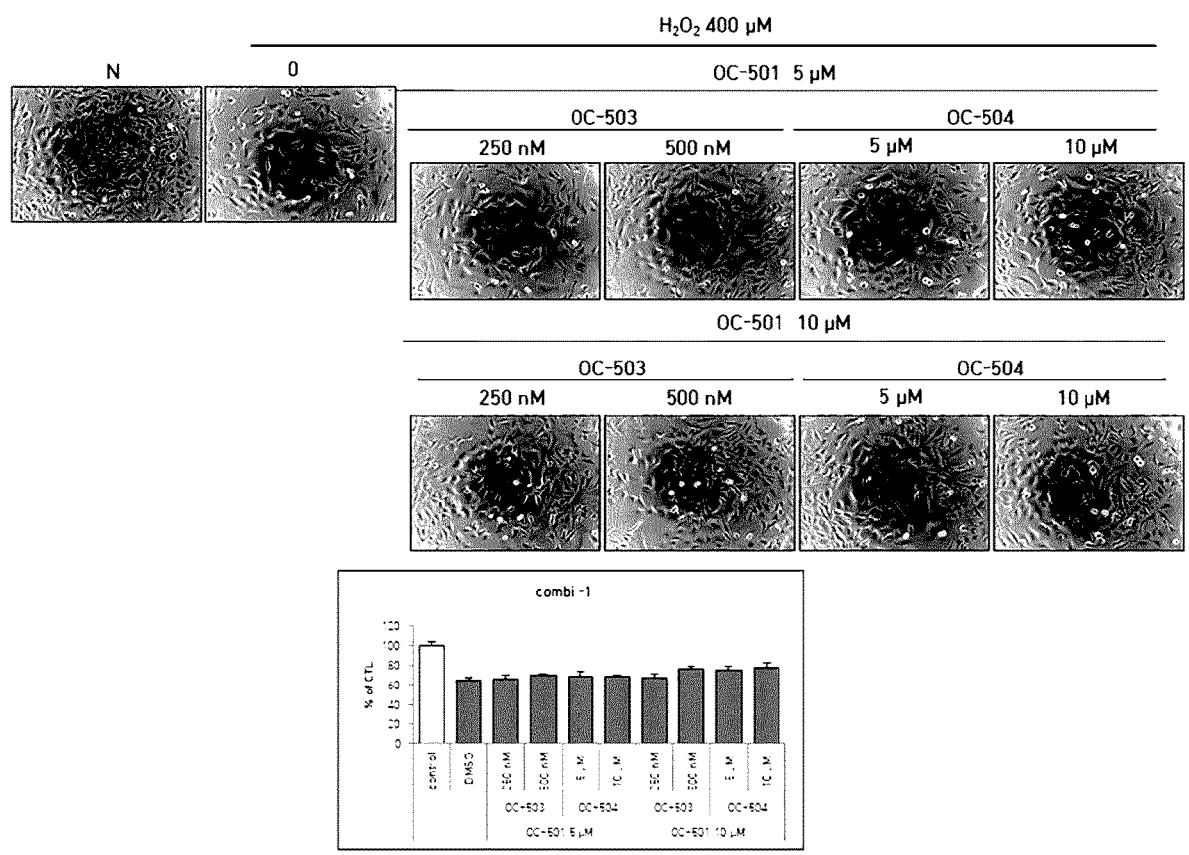
FIG. 11 shows the effect of increasing myoblast proliferation when a combination of dimenhydrinate and harmol or calcium pantothenate is applied.
Figure 12:
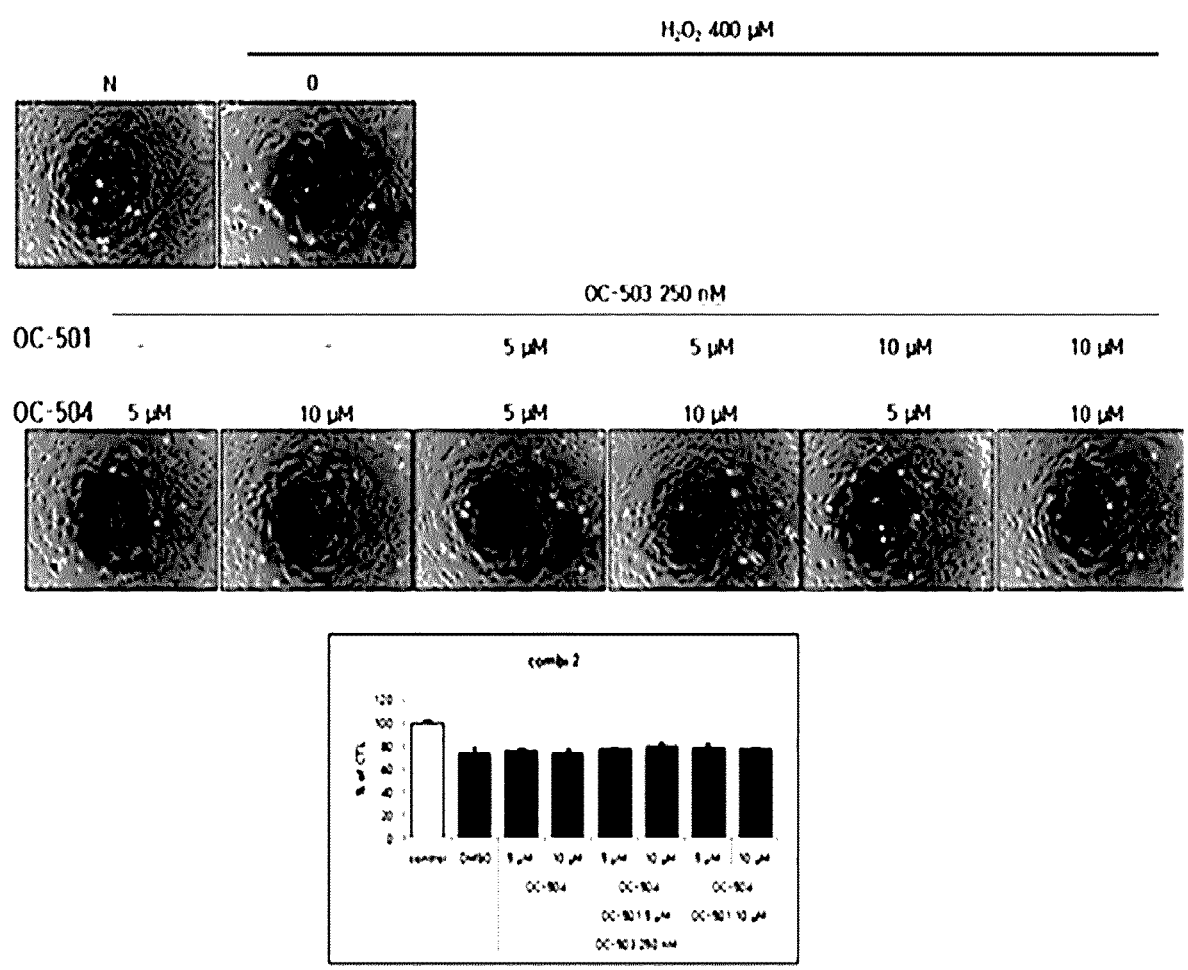
FIG. 12 shows the effect of increasing myoblast proliferation when a combination of dimenhydrinate and harmol or calcium pantothenate is applied.
Figure 13:
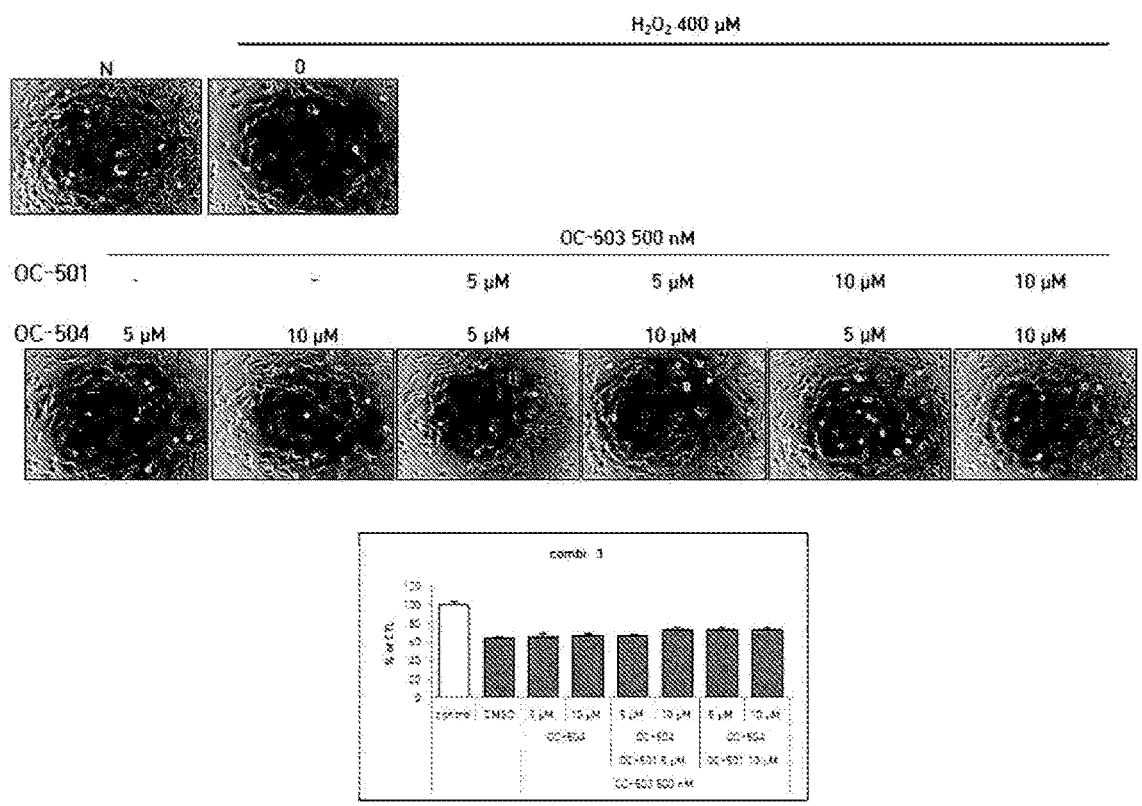
FIG. 13 shows the effect of increasing myoblast proliferation when a combination of harmol and calcium pantothenate, and a combination of dimenhydrinate, harmol and calcium pantothenate are applied.

As a result, it was confirmed that the combinations of dimenhydrinate (OC-501) 10 μM and harmol (OC-503) 500 nM, dimenhydrinate (OC-501) 10 μM and calcium pantothenate (OC-504) 5 dimenhydrinate (OC-501) 10 μM and calcium pantothenate (OC-504) 10 μM, dimenhydrinate (OC-501) 5 μM, harmol (OC-503) 500 nM and calcium pantothenate (OC-504) 10 μM, dimenhydrinate (OC-501) 10 μM, harmol (OC-503) 500 nM and calcium pantothenate (OC-504) 5 μM, dimenhydrinate (OC-501) 10 μM, and harmol (OC-503) 500 nM and calcium pantothenate (OC-504) 10 μM significantly increased myoblast proliferation (FIG. 11 to FIG. 13).

2-3. Identifying Promoting Effects of Myoblast Differentiation by Combination Application Mouse myoblast strain C2C12 was dispensed into 12-well plates at $0.7 \times 10^5$ cells/well and then cultured to a cell density of 70 to 80%. The cells were then washed with PBS and then the medium was replaced with DMEM medium (differentiation medium) containing 2% horse serum, 400 μM $H_2O_2$, and each of following combinations of dimenhydrinate (OC-501), harmol (OC-503), and calcium pantothenate (OC-504): OC-501 5 μM+OC-503 250 nM, OC-501 5 μM+OC-503 500 nM, OC-501 5 μM+OC-504 5 μM, OC-501 5 μM+OC-504 10 μM, OC-501 10 μM+OC-503 250 nM, OC-501 10 μM+OC-503 500 nM, OC-501 10 μM+OC-504 5 μM, OC-501 10 μM+OC-504 10 μM, OC-503 250 nM+OC-504 5 μM, OC-503 250 nM+OC-504 10 μM, OC-503 500 nM+OC-504 5 μM, OC-503 500 nM+OC-504 10 μM, OC-501 5 μM+OC-503 250 nM+OC-504 5 μM, OC-501 5 μM+OC-503 250 nM+OC-504 10 μM, OC-501 10 μM+OC-503 250 nM+OC-504 5 μM, OC-501 10 μM+OC-503 250 nM+OC-504 10 μM, OC-501 5 μM+OC-503 500 nM+OC-504 5 μM, OC-501 5 μM+OC-503 500 nM+OC-504 10 μM, OC-501 10 μM+OC-503 500 nM+OC-504 5 μM, and OC-501 10 μM+OC-503 500 nM+OC-504 10 μM. Differentiation of the myoblast was induced for 5 to 7 days while the replacement of the medium occurred every other day. After the differentiation, cells were identified using a microscope (4× and 10× magnification), and cells were disrupted, and then Western blot analysis was performed using differentiation markers myogenin and myosin heavy chain (MHC) antibodies.

Figure 14:
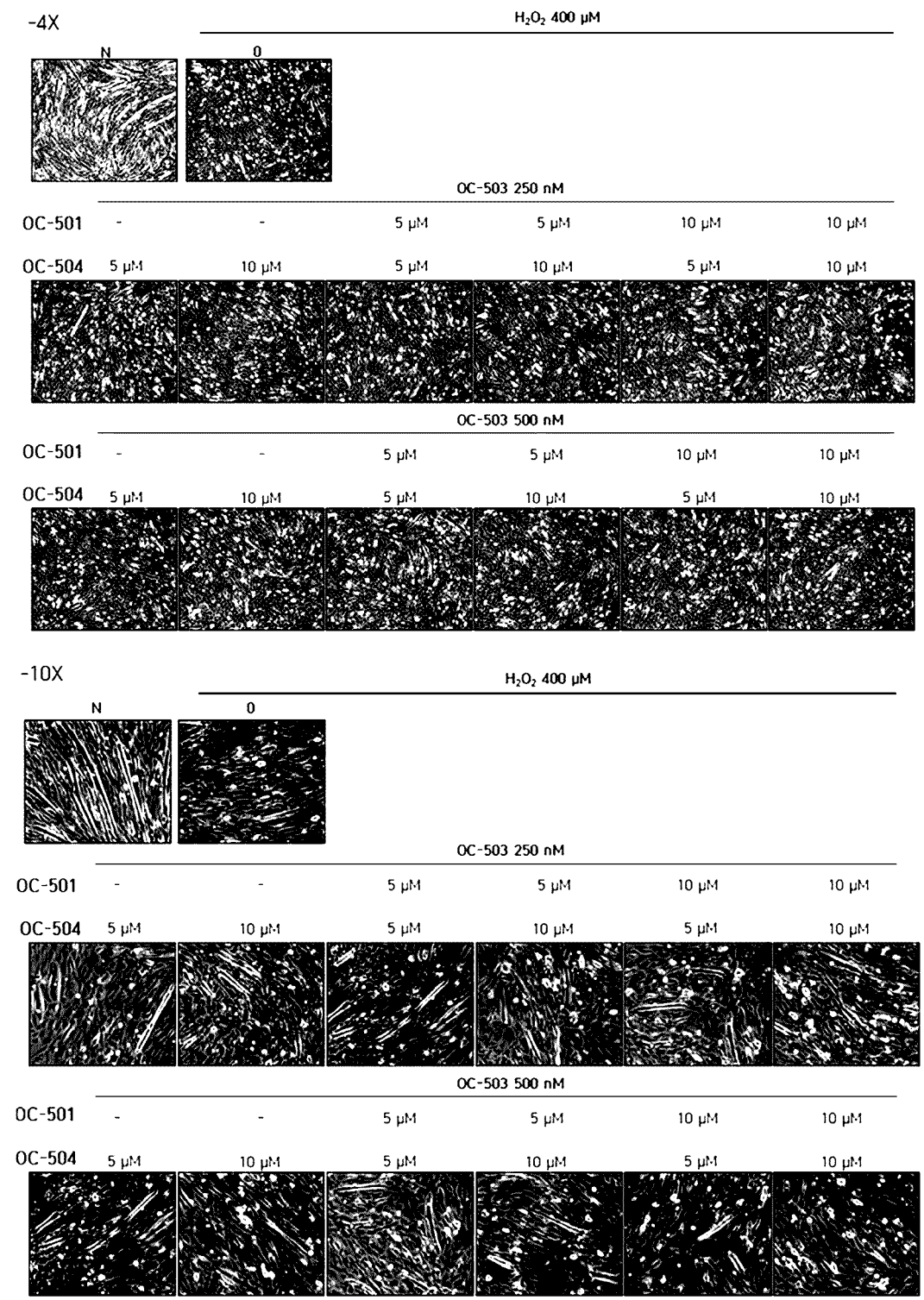
FIG. 14 shows the differentiation effects of myoblasts when a combination of dimenhydrinate and harmol or calcium pantothenate is applied:
Upper: 4× magnification image after differentiation; and
Lower: 10× magnification image after differentiation.
Figure 15:
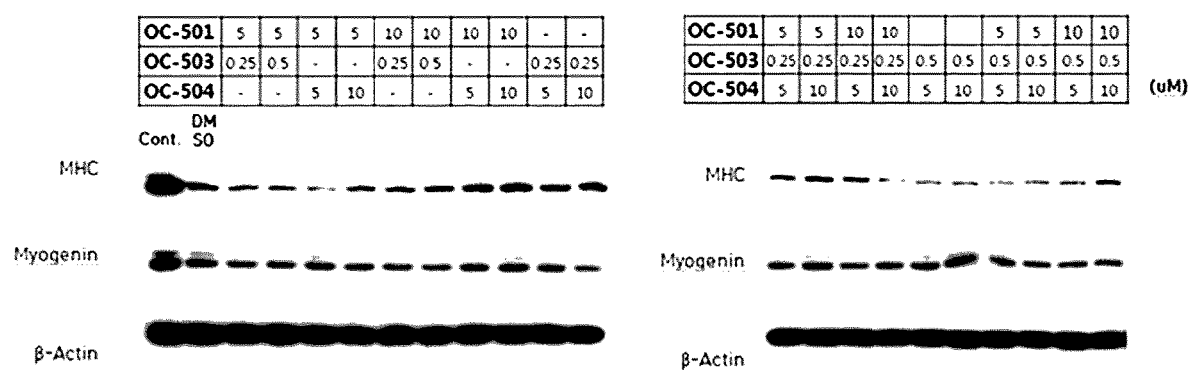
FIG. 15 shows the level of differentiation of myoblast via the expression level of myogenin and MHC as muscle cell differentiation markers in the application of a combination of dimenhydrinate and harmol or calcium pantothenate.

As a result, a combination of dimenhydrinate and calcium pantothenate, and a combination of dimenhydrinate and harmol facilitated differentiation of myoblasts (FIG. 14). In particular, the promotion of differentiation thereof was more markedly increased when applying OC-501 10 μM+OC-504 5 μM, OC-501 10 μM+OC-504 10 μM, OC-503 250 nM+OC-504 5 μM, and OC-503 250 nM+OC-504 10 μM (FIG. 15).

EXAMPLE 3

Identifying Effect by Combination of Dimenhydrinate and Calcium Pantothenate 3-1. Identifying Promoting Effects of Myoblast Differentiation by Combination of Dimenhydrinate and Calcium Pantothenate Mesenchymal stem cells were isolated on day 3 after cobratoxin was inserted into the tibialis anterior muscle of the mouse. Two days after the separation, 10 μM of dimenhydrinate (OC-501) and 5 μM of calcium pantothenate (OC-504) were administered individually or in combination. West blot analysis was performed using differentiation markers PAX7 (paired box protein-7) and MYF5 (Myogenic factor 5) antibodies. After the differentiation, cells were identified using a microscope (4× and 10× magnification).

Figure 16:
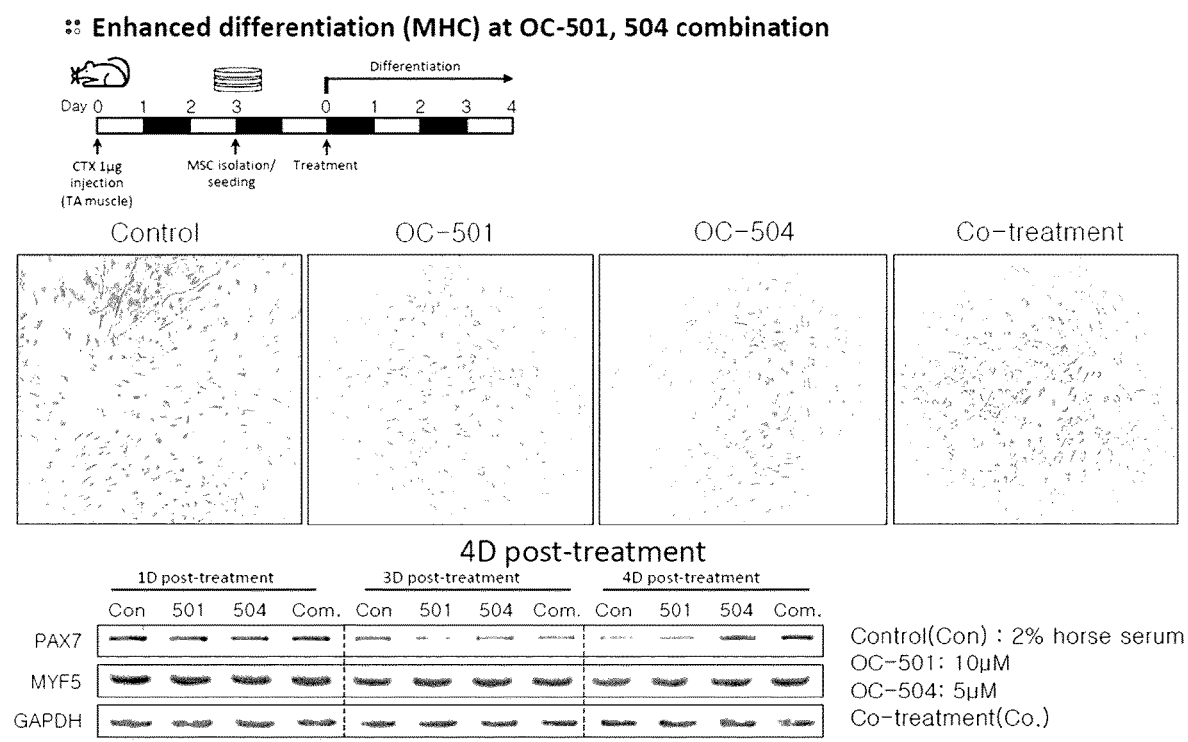
FIG. 16 shows the effects of promoting myoblast differentiation by microscopic and western blot analysis when calcium pantothenate is applied and when a combination of dimenhydrinate and calcium pantothenate is applied.

As a result, 4 days after the application, the expression of PAX7 was increased when applying the calcium pantothenate-treated group and when applying the combination of dimenhydrinate and calcium pantothenate (FIG. 16).

3-2. Identifying Muscle Regeneration Effect by Combination of Dimenhydrinate and Calcium Pantothenate At 3 days after inserting cobratoxin into the tibialis anterior muscle of the mouse, each of dimenhydrinate (OC-501) and calcium pantothenate (OC-504) was applied at 30 mpk (mg/kg) for 3 days, and dimenhydrinate (OC-501) and calcium pantothenate (OC-504) were co-administered such that each content is 15 or 30 mpk (mg/kg) for 3 days. The next day the mice were sacrificed to identify the extent of muscle regeneration.

Figure 17:
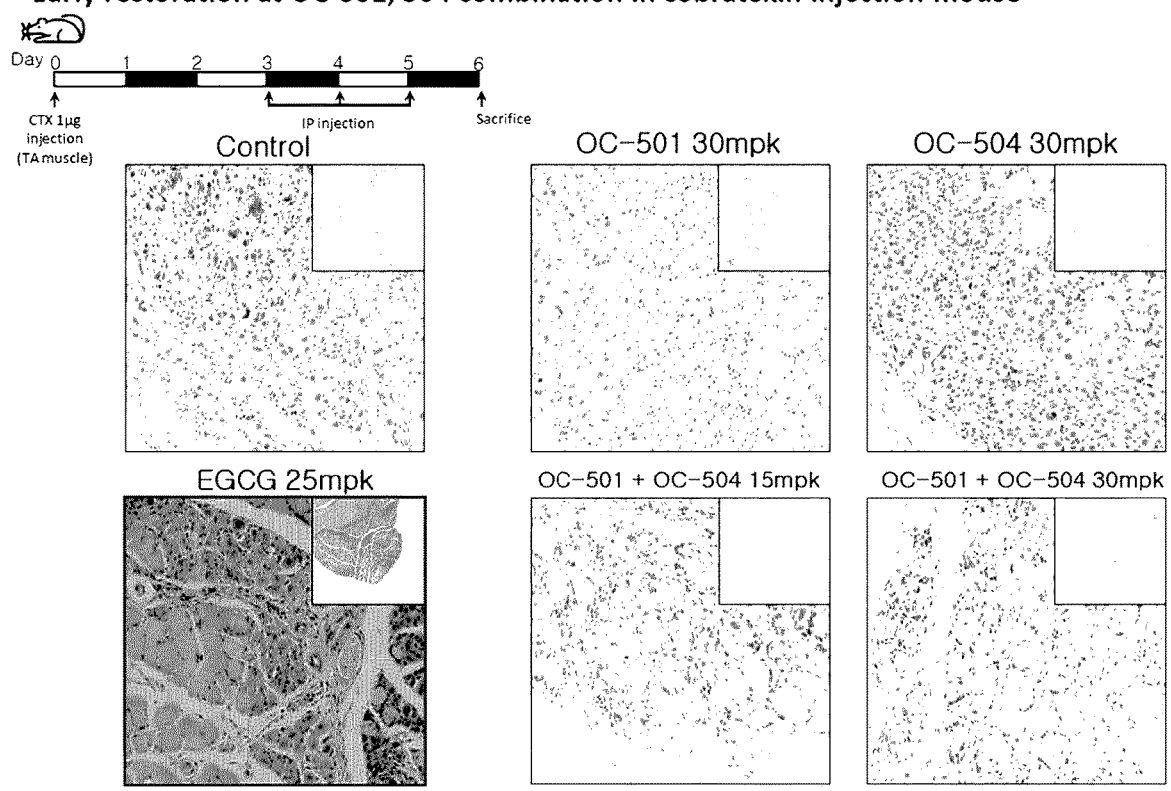
FIG. 17 shows the effect of muscle regeneration via an application of the combination of dimenhydrinate and calcium pantothenate.

As a result, in control mice, myoblasts (dark purple) were just about to start differentiation. In the application of the combination of dimenhydrinate (OC-501) and calcium pantothenate (OC-504), muscle (pink) regeneration was already completed (FIG. 17).

3-3. Identifying Early Recovery of Muscle Fibers by Combination of Dimenhydrinate and Calcium Pantothenate At 3 days after inserting not cobratoxin but cardiotoxin into the tibialis anterior muscle of the mouse, each of dimenhydrinate (OC-501) and calcium pantothenate (OC-504) was applied at 30 mpk (mg/kg), and dimenhydrinate (OC-501) and calcium pantothenate (OC-504) were co-administered such that each content is 15 or 30 mpk (mg/kg). Then, the muscle fiber was identified.

Figure 18:
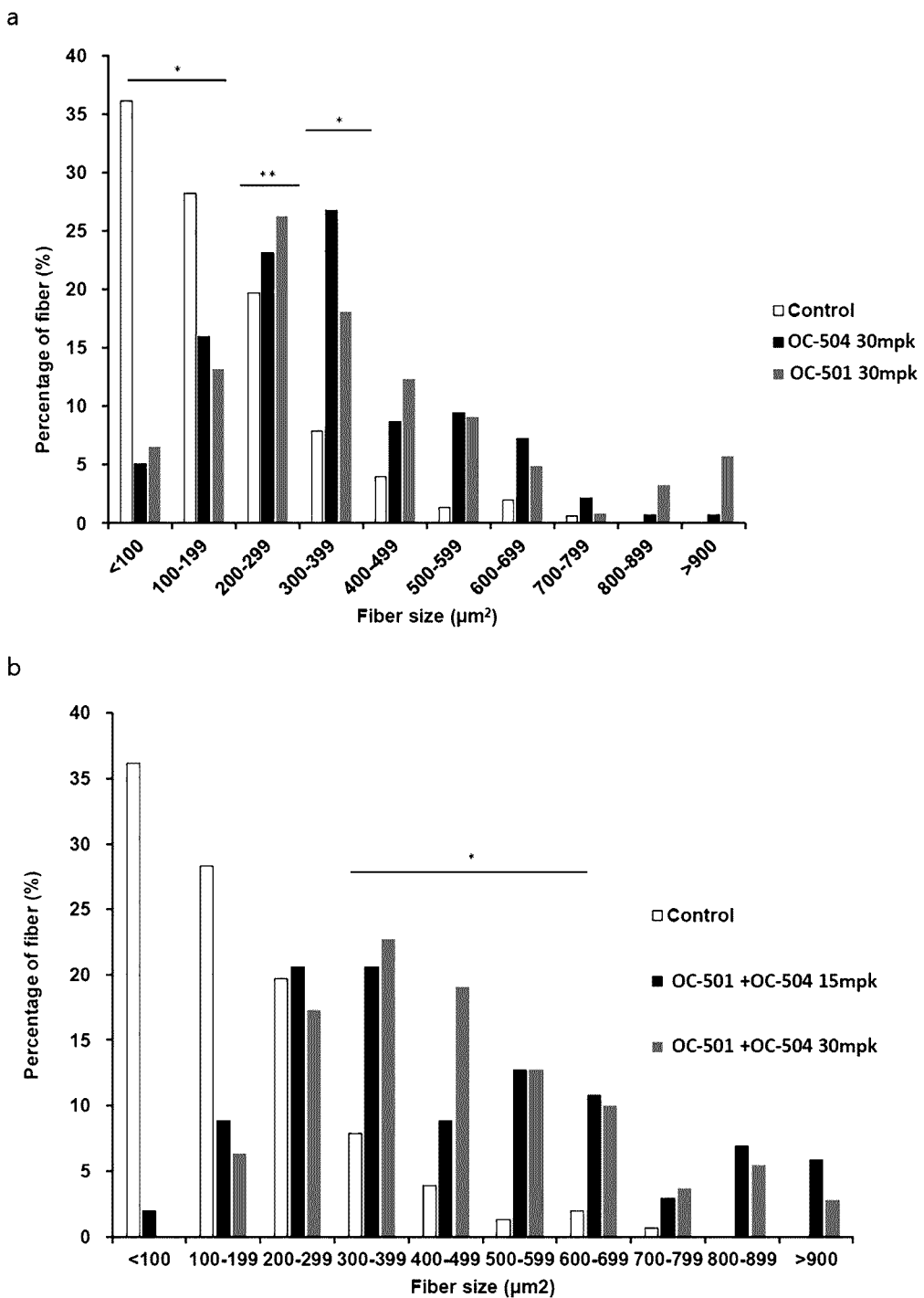
FIG. 18 shows the effect of early recovery of muscle fibers via the application of the combination of dimenhydrinate and calcium pantothenate.

As a result, in the control group, the muscle fibers contracted and mostly showed a size of 200 μm² or smaller. In the application of OC-501 and OC-504 alone and in combination, the muscle fiber size was well sparred (FIG. 18).

Figure 19:
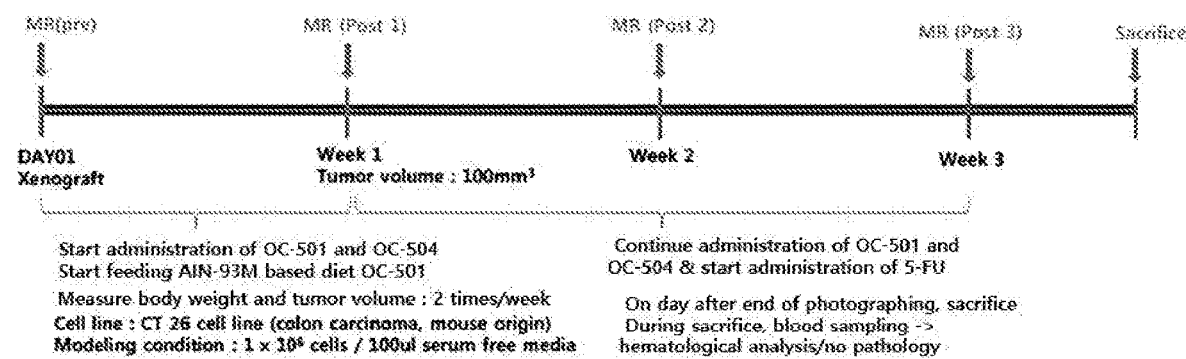
FIG. 19 shows the course of causing cancer-associated sarcopenia and the schedule of administration of the dimenhydrinate and calcium pantothenate therefor.

3-4. Identifying Effect of Combination of Dimenhydrinate and Calcium Pantothenate on Cancer-Associated Muscle and Fat Reduction Cancer-associated sarcopenia was induced by administering 5-FU (5-fluorouracil) as an anticancer agent to mice transplanted with colorectal cancer cells CT26. Further, after the colon cancer cell transplantation, dimenhydrinate (OC-501) and calcium pantothenate (OC-504) were applied thereto alone or in combination. MRI was measured every week to determine muscle and fat changes in OC-501 and 504 alone and combination-treated groups (FIG. 19).

Figure 20:
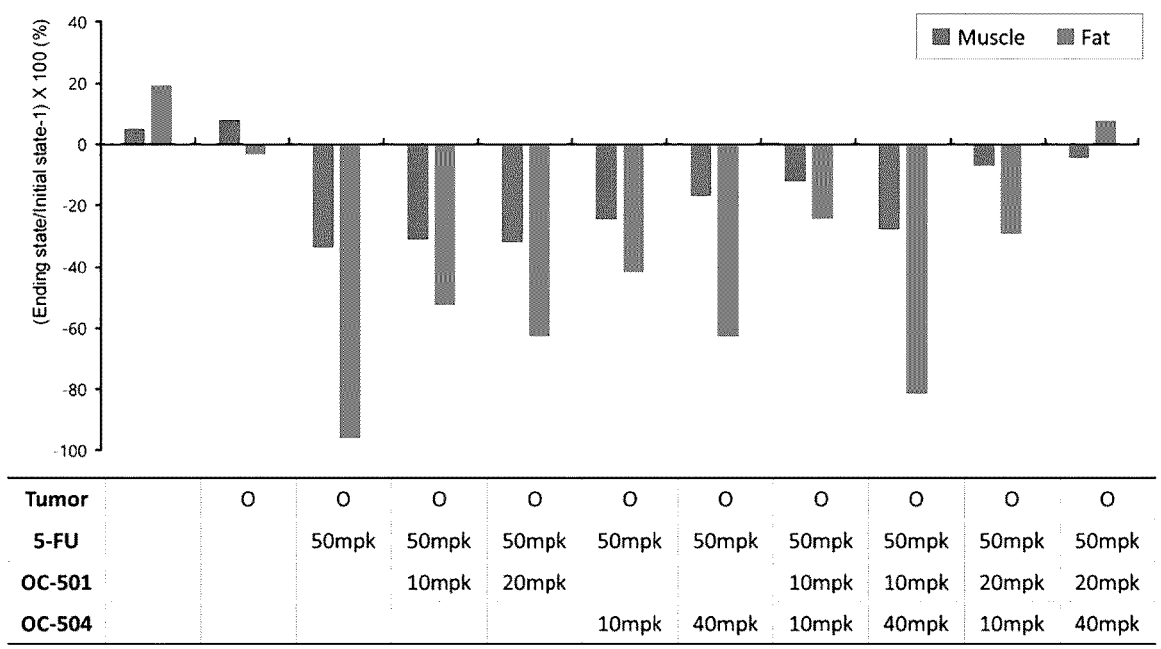
FIG. 20 shows the effects of cancer-associated muscle and fat reduction via the application of the combination of dimenhydrinate and calcium pantothenate.

As a result, sarcopenia was hardly induced in the control mice transplanted with only cancer cells. The muscle amount was decreased by about 40% and the fat was decreased by 95% when the anticancer drug was administered. The muscle mass and fat mass were increased in the groups treated with dimenhydrinate (OC-501) and calcium pantothenate (OC-504) alone or in combination (FIG. 20). In particular, the combination of 20 mpk of dimenhydrinate (OC-501) and 40 mpk of calcium pantothenate (OC-504) recovered muscle and fat levels to a similar degree to the control group.

The invention claimed is:

1. A composition for treating atony, muscular atrophy, muscular dystrophy, myasthenia, cachexia or sarcopenia, or muscle or fat loss caused by administration of an anticancer drug, the composition comprising a combination of dimenhydrinate and calcium pantothenate, wherein the dimenhydrinate is represented by the following Chemical Formula 1:

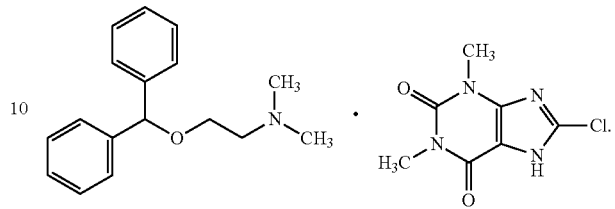

[Chemical Formula 1]

and wherein the calcium pantothenate is represented by the following Chemical Formula 3:

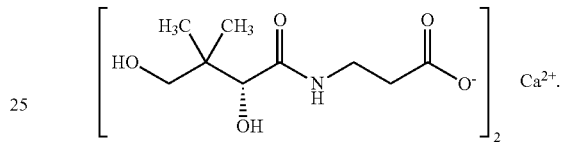

[Chemical Formula 3]

2. The composition of claim 1, wherein the sarcopenia is caused by aging or cancer.

3. The composition of claim 1, further comprising a water-soluble vitamin selected from the group consisting of vitamin C, vitamin B1, vitamin B2, vitamin B6, vitamin H, vitamin PP, pro-vitamin B5 and mixtures thereof.

4. The composition of claim 1, further comprising a fat-soluble vitamin selected from the group consisting of vitamin A, vitamin D, vitamin E, vitamin K1, carotene and mixtures thereof.

5. A composition comprising a combination of dimenhydrinate and harmol, a combination of dimenhydrinate and calcium pantothenate, a combination of harmol and calcium pantothenate, or a combination of dimenhydrinate, harmol and calcium pantothenate.

6. The composition of claim 1, wherein the sarcopenia is caused by aging of cancer.

7. The composition of claim 5, further comprising a water-soluble vitamin selected from the group consisting of vitamin C, vitamin B1, vitamin B2, vitamin B6, vitamin H, vitamin PP, pro-vitamin B5 and mixtures thereof.

8. The composition of claim 5, further comprising a fat-soluble vitamin selected from the group consisting of vitamin A, vitamin D, vitamin E, vitamin K1, carotene and mixtures thereof.

9. A method for treating atony, muscular atrophy, muscular dystrophy, myasthenia, cachexia or sarcopenia, or muscle or fat loss caused by administration of an anticancer drug, comprising administering to a subject in need thereof a composition comprising a combination of dimenhydrinate and calcium pantothenate, wherein the dimenhydrinate is represented by the following Chemical Formula 1:

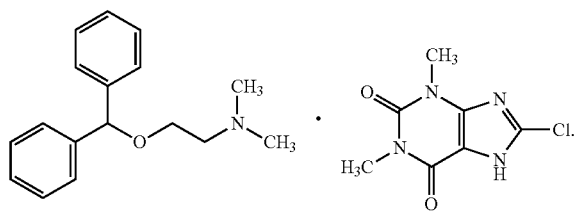

and wherein the calcium pantothenate is represented by the following Chemical Formula 3:

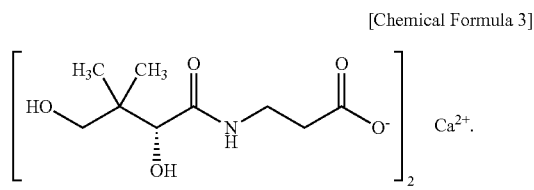

10. The method of claim 9, wherein the sarcopenia is caused by aging or cancer.

11. The method of claim 9, wherein the composition further comprises a water-soluble vitamin selected from the group consisting of vitamin C, vitamin B1, vitamin B2, vitamin B6, vitamin H, vitamin PP, pro-vitamin B5 and mixtures thereof.

12. The method of claim 9, wherein the composition further comprises a fat-soluble vitamin selected from the group consisting of vitamin A, vitamin D, vitamin E, vitamin K1, carotene and mixtures thereof.

13. A method for treating atony, muscular atrophy, muscular dystrophy, myasthenia, cachexia or sarcopenia, or muscle or fat loss caused by administration of an anticancer drug, comprising administering to a subject in need thereof a composition comprising
 a combination of dimenhydrinate and harmol,
 a combination of dimenhydrinate and calcium pantothenate,
 a combination of harmol and calcium pantothenate, or
 a combination of dimenhydrinate, harmol and calcium pantothenate.

14. The method of claim 13, wherein the sarcopenia is caused by aging or cancer.

15. The method of claim 13, wherein the composition further comprises a water-soluble vitamin selected from the group consisting of vitamin C, vitamin B1, vitamin B2, vitamin B6, vitamin H, vitamin PP, pro-vitamin B5 and mixtures thereof.

16. The method of claim 13, wherein the composition further comprises a fat-soluble vitamin selected from the group consisting of vitamin A, vitamin D, vitamin E, vitamin K1, carotene and mixtures thereof.

* * * * *